(12) United States Patent
Moriwaki et al.

(10) Patent No.: US 8,502,209 B2
(45) Date of Patent: Aug. 6, 2013

(54) POLYMER COMPOUND AND ORGANIC TRANSISTOR USING THE SAME

(75) Inventors: Shota Moriwaki, Ibaraki (JP); Osamu Goto, Tsukuba (JP); Tomoko Takasuka, Hachioji (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 296 days.

(21) Appl. No.: 12/995,570

(22) PCT Filed: May 28, 2009

(86) PCT No.: PCT/JP2009/060204
§ 371 (c)(1),
(2), (4) Date: Dec. 1, 2010

(87) PCT Pub. No.: WO2009/148103
PCT Pub. Date: Dec. 10, 2009

(65) Prior Publication Data
US 2011/0073854 A1    Mar. 31, 2011

(30) Foreign Application Priority Data
Jun. 5, 2008    (JP) ................................. 2008-147850

(51) Int. Cl.
*H01L 51/00* (2006.01)
*H01L 51/40* (2006.01)
*H01L 29/08* (2006.01)

(52) U.S. Cl.
USPC .................. 257/40; 257/E51.018; 438/99

(58) Field of Classification Search
USPC ........................ 257/49, 40; 439/99
See application file for complete search history.

(56) References Cited

U.S. PATENT DOCUMENTS

| | | | |
|---|---|---|---|
| 5,308,851 A | 5/1994 | Teleha et al. | |
| 5,594,001 A | 1/1997 | Teleha et al. | |
| 5,990,132 A * | 11/1999 | Teleha et al. | 514/333 |
| 2003/0172774 A1* | 9/2003 | Naito et al. | 75/244 |
| 2006/0009614 A1* | 1/2006 | Yamahara et al. | 528/380 |
| 2006/0102890 A1* | 5/2006 | Yamahara et al. | 257/40 |
| 2007/0228359 A1* | 10/2007 | Heim et al. | 257/40 |
| 2009/0127547 A1* | 5/2009 | Luebben et al. | 257/40 |
| 2010/0090206 A1* | 4/2010 | Nakatani et al. | 257/40 |
| 2010/0178481 A1* | 7/2010 | George et al. | 428/213 |
| 2011/0133174 A1* | 6/2011 | Jia | 257/40 |

FOREIGN PATENT DOCUMENTS

| | | |
|---|---|---|
| JP | 8-509713 A | 10/1996 |
| WO | WO 02/45184 A1 | 6/2002 |
| WO | WO 2005049695 A1 * | 6/2005 |

OTHER PUBLICATIONS

K. Wong, et al; "Modulation of Physical Properties of Ter(9,9-ditolylfluorene) by Backbone-Embeded Heteroarenes"; Organic Letters; vol. 8, No. 7; 2006, pp. 1415-1418.
D. MacDowell, et al; "The Chemistry of Indenothiophenes, II. 4H-Indeno[1,2-*b*]thiophene and 8H-Indeno[1,2-c]thiophene"; Journal. Organic Chemistry; vol. 35, No. 4; 1970; pp. 871-875.
C. Zhao, et al; "Derivatives of 4,9-Dihydro-*s*-indaceno{1,2-*b*'}dithiophene-4,9-dione: Synthesis and Properties"; Journal Organic. Chemistry, vol. 72, 2007, pp. 6364-6371.
L. Pouchain, et al; "Quaterthiophenes with Terminal Indeno[1,2-*b*]thiophene Units as *p*-Type Organic Semiconductors"; Journal Organic. Chemistry, vol. 74, 2009, pp. 1054-1064.
S. Chan; "Synthesis Characterization, and Photovoltaic Properties of Novel Semiconducting Polymers with Thiophene-Phenylene-Thiophene (TPT) as Coplanar Units"; Macromolecules, vol. 41, 2008; pp. 5519-5526.
International Preliminary Report on Patentability and Written Opinion issued Jan. 20, 2011 in International Application No. PCT/JP2009/060204 to Sumitomo Chemical Co., Ltd.

* cited by examiner

*Primary Examiner* — Robert J Hoffberg
*Assistant Examiner* — Igwe U Anya
(74) *Attorney, Agent, or Firm* — Sughrue Mion, PLLC

(57) ABSTRACT

A polymer compound comprising a repeating unit represented by the formula (I):

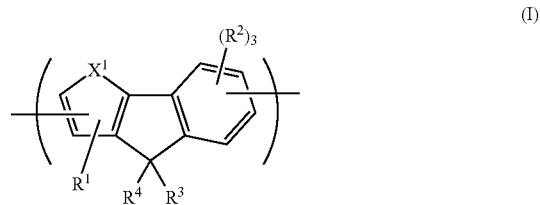

(I)

[wherein $X^1$ represents an oxygen atom, a sulfur atom or $N(R^N)$—, $R^1$ to $R^4$ and $R^N$ represent a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group or the like.].

17 Claims, No Drawings

POLYMER COMPOUND AND ORGANIC TRANSISTOR USING THE SAME

CROSS REFERENCE TO RELATED APPLICATIONS

This application is a National Stage of International Application No. PCT/JP2009/060204, filed on May 28, 2009, which claims priority from Japanese Patent Application No. 2008-147850, filed on Jun. 5, 2008, the contents of all of which are incorporated herein by reference in their entirety.

TECHNICAL FIELD

The present invention relates to a polymer compound and an organic transistor using the same.

BACKGROUND ART

As materials used in organic transistors, various polymer compounds are investigated, and a polymer compound containing the following fluorenediyl group and the following triphenylamine residue as a repeating unit is known (see, International Publication WO 02/45184 pamphlet) as an example thereof.

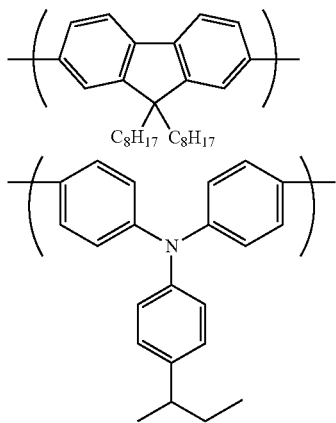

DISCLOSURE OF THE INVENTION

When the above-described polymer compound is used in an electric field effect type organic transistor, however, its electric field effect mobility is not sufficient yet.

The present invention has an object of providing a polymer compound which is capable of producing an electric field effect type organic transistor excellent in electric field effect mobility.

The present invention provides, in a first aspect, a polymer compound comprising a repeating unit represented by the formula (I):

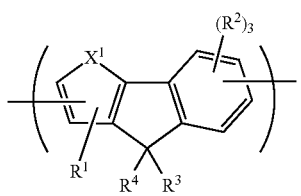

(I)

[wherein $X^1$ represents an oxygen atom, a sulfur atom or $-N(R^N)-$, $R^1$, $R^2$ and $R^N$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group, $R^3$ and $R^4$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group. A plurality of $R^2$s may be the same or mutually different.]

The present invention provides, in a second aspect, a compound represented by the formula (V).

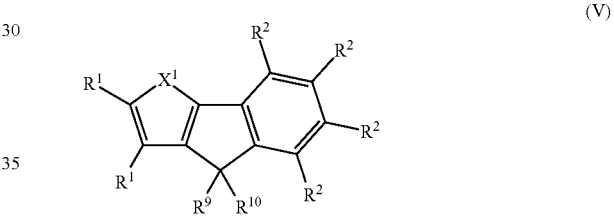

(V)

[wherein $X^1$ represents an oxygen atom, a sulfur atom or $-N(R^N)-$, $R^1$, $R^2$ and $R^N$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group, $R^9$ and $R^{10}$ represent each independently a hydrogen atom, a halogen atom, an alkyl group, an alkenyl group, an alkynyl group, an alkoxy group, an alkylthio group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group. A plurality of $R^1$s may be the same or mutually different, and a plurality of $R^2$s may be the same or mutually different.].

The present invention provides, in a third aspect, a method of producing a compound represented by the formula (M-1-3a), comprising a first step of reacting a compound represented by the formula (M-1-1a) and a compound represented by the formula (M-1-1b) to produce a compound represented by the formula (M-1-2a), and a second step of subjecting the compound represented by the formula (M-1-2a) to a dehydration reaction to produce a compound represented by the formula (M-1-3a).

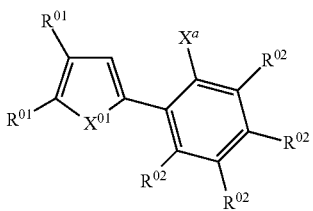

(M-1-1a)

[wherein $X^a$ represents a halogen atom, $X^{01}$ represents an oxygen atom, a sulfur atom or —N($R^{NN}$)—, $R^{01}$, $R^{02}$ and $R^{NN}$ represent each independently a hydrogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, a substituted amino group, a silyl group, a substituted silyl group, an imine residue, an acid imide group, a cyano group or a nitro group. A plurality of $R^{01}$s may be the same or mutually different, and a plurality of $R^{02}$s may be the same or mutually different.]

$$R^{11}-C(=O)-R^{12} \quad \text{(M-1-1b)}$$

[wherein $R^{11}$ and $R^{12}$ represent each independently a hydrogen atom, an alkyl group, an alkenyl group, an alkynyl group, an alkylthio group, an aryl group, an arylthio group, an arylalkyl group, an arylalkylthio group, an arylalkenyl group, an arylalkynyl group, a mono-valent heterocyclic group, a heterocyclic thio group, an amino group, a substituted amino group, a silyl group, a substituted silyl group, an imine residue, an amide group, an acid imide group, a cyano group or a nitro group.]

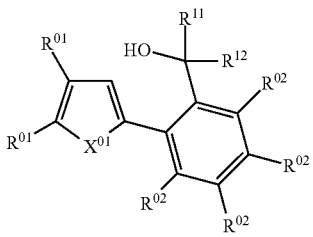

(M-1-2a)

[wherein $X^{01}$, $R^{01}$, $R^{02}$, $R^{11}$ and $R^{12}$ represent the same meaning as described above.]

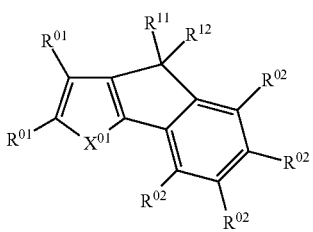

(M-1-3a)

[wherein $X^{01}$, $R^{01}$, $R^{02}$, $R^{11}$ and $R^{12}$ represent the same meaning as described above.].

The present invention provides, in a fourth aspect, a composition comprising the above-described polymer compound.

The present invention provides, in a fifth aspect, a film comprising the above-described polymer compound.

The present invention provides, in a sixth aspect, a polymer light emitting device comprising an anode, a cathode, and an organic layer containing the above-described polymer compound disposed between the anode and the cathode.

The present invention provides, in a seventh aspect, an organic transistor comprising a source electrode, a drain electrode, a gate electrode, and an organic layer containing the above-described polymer compound.

The present invention provides, in an eighth aspect, a photoelectric conversion device comprising an anode, a cathode, and an organic layer containing the above-described polymer compound disposed between the anode and the cathode.

The present invention provides, in a ninth aspect, a film comprising the above-described compound.

The present invention provides, in a tenth aspect, a light emitting device comprising an anode, a cathode, and an organic layer containing the above-described compound disposed between the anode and the cathode.

MODES FOR CARRYING OUT THE INVENTION

The polymer compound of the present invention comprises a repeating unit represented by the formula (I).

In the formula (I), $X^1$ represents an oxygen atom, a sulfur atom or —N($R^N$)—, $R^1$, $R^2$ and $R^N$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group. $R^3$ and $R^4$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group. A plurality of $R^2$s may be the same or mutually different.

$R^1$, $R^2$ and $R^N$ represent preferably a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group. $R^3$ and $R^4$ represent preferably a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group.

The halogen atom includes a fluorine atom, a chlorine atom, a bromine atom and an iodine atom. The alkyl group may be linear or branched, and may also be a cycloalkyl group. The alkyl group has a carbon atom number of usually 1 to 20. Examples of the alkyl group include a methyl group, an ethyl group, a n-propyl group, an isopropyl group, a n-butyl group, an isobutyl group, a t-butyl group, a s-butyl group, a 3-methylbutyl group, a n-pentyl group, a n-hexyl group, a 2-ethylhexyl group, a n-heptyl group, a n-octyl group, a n-nonyl group, a n-decyl group, a 3,7-dimethyloctyl group and a n-lauryl group. A hydrogen atom in the above-described alkyl group is optionally substituted by a fluorine atom, a chlorine atom, a bromine atom or an iodine atom (preferably, a fluorine atom). The substituted alkyl group includes a trifluoromethyl group, a pentafluoroethyl group, a perfluorobutyl group, a perfluorohexyl group, a perfluorooctyl group and the like.

The alkenyl group may be linear or branched, and may also be a cycloalkenyl group. The alkenyl group has a carbon atom number of usually 2 to 20. Examples of the alkenyl group include an ethenyl group, a propenyl group, a 2-propenyl group, a 1-methylpropenyl group, a 2-methylpropenyl group, a 1,2-dimethylpropenyl group, a butenyl group, a 2-methylbutenyl group, a 1,3-butadienyl group, a pentenyl group, a hexenyl group, a cyclohexenyl group, a heptenyl group, an octenyl group and a 2-ethylhexenyl group. A hydrogen atom in the above-described alkenyl group is optionally substituted by a fluorine atom, a chlorine atom, a bromine atom or an iodine atom. The substituted alkenyl group includes a trifluoroethenyl group, a perfluorobutenyl group, a perfluorohexenyl group, a perfluorooctenyl group and the like.

The alkynyl group may be linear or branched, and may also be a cycloalkynyl group. The alkynyl group has a carbon atom number of usually 2 to 20. Examples of the alkynyl group include an ethynyl group, a propynyl group, a 2-propynyl group, a 2-methylpropynyl group, a butynyl group, a 2-methylbutynyl group, a 1,3-butanediyl group, a pentynyl group, a hexynyl group, a cyclohexynyl group, a heptynyl group, an octynyl group and a 2-ethylhexynyl group. A hydrogen atom in the above-described alkynyl group is optionally substituted by a fluorine atom, a chlorine atom, a bromine atom or an iodine atom. The substituted alkynyl group includes a fluoroethynyl group, a perfluorobutynyl group, a perfluorohexynyl group, a perfluorooctynyl group and the like.

The alkoxy group may be linear or branched, and may also be a cycloalkyloxy group. The alkoxy group has a carbon atom number of usually 1 to 20. Examples of the alkoxy group include a methoxy group, an ethoxy group, a n-propyloxy group, an isopropyloxy group, a n-butoxy group, an isobutoxy group, a s-butoxy group, a t-butoxy group, a n-pentyloxy group, a n-hexyloxy group, a cyclohexyloxy group, a n-heptyloxy group, a n-octyloxy group, a 2-ethylhexyloxy group, a n-nonyloxy group, a n-decyloxy group, a 3,7-dimethyloctyloxy group and a n-lauryloxy group. A hydrogen atom in the above-described alkoxy group is optionally substituted by a fluorine atom, a chlorine atom, a bromine atom or an iodine atom (preferably, a fluorine atom). The substituted alkoxy group includes a trifluoromethoxy group, a pentafluoroethoxy group, a perfluorobutoxy group, a perfluorohexyl group, a perfluorooctyl group and the like.

The alkylthio group may be linear or branched, and may also be a cycloalkylthio group. The alkylthio group has a carbon atom number of usually 1 to 20. Examples of the alkylthio group include a methylthio group, an ethylthio group, a n-propylthio group, an isopropylthio group, a n-butylthio group, an isobutylthio group, a s-butylthio group, a t-butylthio group, a n-pentylthio group, a n-hexylthio group, a cyclohexylthio group, a n-heptylthio group, a n-octylthio group, a 2-ethylhexylthio group, a n-nonylthio group, a n-decylthio group, a 3,7-dimethyloctylthio group and a n-laurylthio group. A hydrogen atom in the above-described alkylthio group is optionally substituted by a fluorine atom, a chlorine atom, a bromine atom or an iodine atom (preferably, a fluorine atom). The substituted alkylthio group includes a trifluoromethylthio group and the like.

The aryl group means an atomic group obtained by removing one hydrogen atom from an aromatic hydrocarbon, and includes also those having a condensed ring, and those having two or more independent benzene rings or condensed rings bonded directly or via a group such as vinylene and the like. The aryl group has a carbon atom number of usually 6 to 60, preferably 6 to 48. The above-described aryl group optionally has a substituent. This substituent includes linear or branched alkyl groups having a carbon atom number of 1 to 20, cycloalkyl groups having a carbon atom number of 1 to 20, alkoxy groups containing in its structure a linear or branched alkyl group having a carbon atom number of 1 to 20 or a cycloalkyl group having a carbon atom number of 1 to 20, groups represented by the following formula (5), and the like. Examples of the aryl group include a phenyl group, a $C_1$ to $C_{12}$ alkoxyphenyl group ($C_1$ to $C_{12}$ means that the carbon atom number thereof is 1 to 12; the same shall apply hereinafter), a $C_1$ to $C_{12}$ alkylphenyl group, a 1-naphthyl group, a 2-naphthyl group, a 1-anthracenyl group, a 2-anthracenyl group, a 9-anthracenyl group and a pentafluorophenyl group, and preferable are a $C_1$ to $C_{12}$ alkoxyphenyl group and a $C_1$ to $C_{12}$ alkylphenyl group.

Examples of the $C_1$ to $C_{12}$ alkoxyphenyl group include a methoxyphenyl group, an ethoxyphenyl group, a n-propyloxyphenyl group, an isopropyloxyphenyl group, a n-butoxyphenyl group, an isobutoxyphenyl group, a s-butoxyphenyl group, a t-butoxyphenyl group, a n-pentyloxyphenyl group, a n-hexyloxyphenyl group, a cyclohexyloxyphenyl group, a n-heptyloxyphenyl group, a n-octyloxyphenyl group, a 2-ethylhexyloxyphenyl group, a n-nonyloxyphenyl group, a n-decyloxyphenyl group, a 3,7-dimethyloctyloxyphenyl group, a n-lauryloxyphenyl group, and the like.

Examples of the $C_1$ to $C_{12}$ alkylphenyl group include a methylphenyl group, an ethylphenyl group, a dimethylphenyl group, a n-propylphenyl group, a mesityl group, a methylethylphenyl group, an isopropylphenyl group, a n-butylphenyl group, an isobutylphenyl group, a s-butylphenyl group, a t-butylphenyl group, a n-pentylphenyl group, an isoamylphenyl group, a hexylphenyl group, a n-heptylphenyl group, a n-octylphenyl group, a n-nonylphenyl group, a n-decylphenyl group, a n-dodecylphenyl group, and the like.

A hydrogen atom in the above-described aryl group is optionally substituted by a fluorine atom, a chlorine atom, a bromine atom or an iodine atom (preferably, a fluorine atom).

$$—O—(CH_2)_{g1}—O—(CH_2)_{h1}—CH_3 \qquad (5)$$

(wherein g1 represents an integer of 1 to 6, and h1 represents an integer of 0 to 5.).

The aryloxy group has a carbon atom number of usually 6 to 60, preferably 6 to 48. Examples of the aryloxy group include a phenoxy group, a $C_1$ to $C_{12}$ alkoxyphenoxy group, a $C_1$ to $C_{12}$ alkylphenoxy group, a 1-naphthyloxy group, a 2-naphthyloxy group and a pentafluorophenyloxy group, and preferable are a $C_1$ to $C_{12}$ alkoxyphenoxy group and a $C_1$ to $C_{12}$ alkylphenoxy group.

Examples of the $C_1$ to $C_{12}$ alkoxyphenoxy group include a methoxyphenoxy group, an ethoxyphenoxy group, a n-propyloxyphenoxy group, an isopropyloxyphenoxy group, a n-butoxyphenoxy group, an isobutoxyphenoxy group, a s-butoxyphenoxy group, a t-butoxyphenoxy group, a n-pentyloxyphenoxy group, a n-hexyloxyphenoxy group, a cyclohexyloxyphenoxy group, a n-heptyloxyphenoxy group, a n-octyloxyphenoxy group, a 2-ethylhexyloxyphenoxy group, a n-nonyloxyphenoxy group, a n-decyloxyphenoxy group, a 3,7-dimethyloctyloxyphenoxy group, a n-lauryloxyphenoxy group and the like.

Examples of the $C_1$ to $C_{12}$ alkylphenoxy group include a methylphenoxy group, an ethylphenoxy group, a dimethylphenoxy group, a n-propylphenoxy group, a 1,3,5-trimethylphenoxy group, a methylethylphenoxy group, an isopropylphenoxy group, a n-butylphenoxy group, an isobutylphenoxy group, a s-butylphenoxy group, a t-butylphenoxy group, a n-pentylphenoxy group, an isoamylphenoxy group, a n-hexylphenoxy group, a n-heptylphenoxy group, a n-octylphenoxy group, a n-nonylphenoxy group, a n-decylphenoxy group, a n-dodecylphenoxy group and the like.

The arylthio group optionally has a substituent on its aromatic ring, and has a carbon atom number of usually 6 to 60. Examples of the arylthio group include a phenylthio group, a $C_1$ to $C_{12}$ alkoxyphenylthio group, a $C_1$ to $C_{12}$ alkylphenylthio group, a 1-naphthylthio group, a 2-naphthylthio group, a pentafluorophenylthio group, a pyridylthio group, a pyridazinylthio group, a pyrimidylthio group, a pyrazylthio group and a triazylthio group.

The arylalkyl group optionally has a substituent, and has a carbon atom number of usually 7 to 60. Examples of the arylalkyl group include a phenyl $C_1$ to $C_{12}$ alkyl group, a $C_1$ to $C_{12}$ alkoxyphenyl $C_1$ to $C_{12}$ alkyl group, a $C_1$ to $C_{12}$ alkylphenyl $C_1$ to $C_{12}$ alkyl group, a 1-naphthyl $C_1$ to $C_{12}$ alkyl group and a 2-naphthyl $C_1$ to $C_{12}$ alkyl group.

The arylalkoxy group optionally has a substituent, and has a carbon atom number of usually 7 to 60. Examples of the arylalkoxy group include a phenyl $C_1$ to $C_{12}$ alkoxy group, a $C_1$ to $C_{12}$ alkoxyphenyl $C_1$ to $C_{12}$ alkoxy group, a $C_1$ to $C_{12}$ alkylphenyl $C_1$ to $C_{12}$ alkoxy group, a 1-naphthyl $C_1$ to $C_{12}$ alkoxy group and a 2-naphthyl $C_1$ to $C_{12}$ alkoxy group.

The arylalkylthio group optionally has a substituent, and has a carbon atom number of usually 7 to 60. Examples of the arylalkylthio group include a phenyl $C_1$ to $C_{12}$ alkylthio group, a $C_1$ to $C_{12}$ alkoxyphenyl $C_1$ to $C_{12}$ alkylthio group, a $C_1$ to $C_{12}$ alkylphenyl $C_1$ to $C_{12}$ alkylthio group, a 1-naphthyl $C_1$ to $C_{12}$ alkylthio group and a 2-naphthyl $C_1$ to $C_{12}$ alkylthio group.

The arylalkenyl group has a carbon atom number of usually 8 to 60. Examples of the arylalkenyl group include a phenyl $C_2$ to $C_{12}$ alkenyl group, a $C_1$ to $C_{12}$ alkoxyphenyl $C_2$ to $C_{12}$ alkenyl group, a $C_1$ to $C_{12}$ alkylphenyl $C_2$ to $C_{12}$ alkenyl group, a 1-naphthyl $C_2$ to $C_{12}$ alkenyl group and a 2-naphthyl $C_2$ to $C_{12}$ alkenyl group, and preferable are a $C_1$ to $C_{12}$ alkoxyphenyl $C_2$ to $C_{12}$ alkenyl group and a $C_1$ to $C_{12}$ alkylphenyl $C_2$ to $C_{12}$ alkenyl group.

The arylalkynyl group has a carbon atom number of usually 8 to 60. Examples of the arylalkynyl group include a phenyl $C_2$ to $C_{12}$ alkynyl group, a $C_1$ to $C_{12}$ alkoxyphenyl $C_2$ to $C_{12}$ alkynyl group, a $C_1$ to $C_{12}$ alkylphenyl $C_2$ to $C_{12}$ alkynyl group, a 1-naphthyl $C_2$ to $C_{12}$ alkynyl group and a 2-naphthyl $C_2$ to $C_{12}$ alkynyl group, and preferable are a $C_1$ to $C_{12}$ alkoxyphenyl $C_2$ to $C_{12}$ alkynyl group and a $C_1$ to $C_{12}$ alkylphenyl $C_2$ to $C_{12}$ alkynyl group.

The mono-valent heterocyclic group means an atomic group remaining after removing one hydrogen atom from a heterocyclic compound. The carbon atom number of the mono-valent heterocyclic group is usually 4 to 60, preferably 4 to 20. The carbon atom number of the mono-valent heterocyclic group does not include the carbon atom number of the substituent. The above-described heterocyclic compound refers to organic compounds having a cyclic structure in which elements constituting the ring include not only a carbon atom, but also a hetero atom such as oxygen, sulfur, nitrogen, phosphorus, boron, silicon and the like contained in the ring. Examples of the mono-valent heterocyclic group include a thienyl group, a $C_1$ to $C_{12}$ alkylthienyl group, a pyrrolyl group, a furyl group, a pyridyl group, a $C_1$ to $C_{12}$ alkylpyridyl group, a piperidyl group, a quinolyl group and an isoquinolyl group, and preferable are a thienyl group, a $C_1$ to $C_{12}$ alkylthienyl group, a pyridyl group and a $C_1$ to $C_{12}$ alkylpyridyl group. Of the mono-valent heterocyclic groups, mono-valent aromatic heterocyclic groups are preferable.

The heterocyclic thio group means a group obtained by substituting a hydrogen atom of a mercapto group by a mono-valent heterocyclic group. The heterocyclic thio group includes hetero arylthio groups such as a pyridylthio group, a pyridazinylthio group, a pyrimidylthio group, a pyrazinylthio group, a triazinylthio group and the like.

The substituted amino group includes amino groups substituted by one or two groups selected from the group consisting of an alkyl group, an alkenyl group, an alkynyl group, an aryl group, an arylalkyl group and a mono-valent heterocyclic group, and preferable are amino groups substituted by one or two groups selected from the group consisting of an alkyl group, an aryl group, an arylalkyl group and a mono-valent heterocyclic group. The alkyl group, alkenyl group, alkynyl group, aryl group, arylalkyl group and mono-valent heterocyclic group optionally have a substituent. The carbon atom number of the substituted amino group is usually 1 to 60, preferably 2 to 48, not including the carbon atom number of the substituent. Examples of the substituted amino group include a methylamino group, a dimethylamino group, an ethylamino group, a diethylamino group, a n-propylamino group, a di-n-propylamino group, an isopropylamino group, a diisopropylamino group, a n-butylamino group, a s-butylamino group, an isobutylamino group, a t-butylamino group, a n-pentylamino group, a n-hexylamino group, a cyclohexylamino group, a n-heptylamino group, a n-octylamino group, a 2-ethylhexylamino group, a n-nonylamino group, a n-decylamino group, a 3,7-dimethyloctylamino group, a n-laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a $C_1$ to $C_{12}$ alkoxyphenylamino group, a di ($C_1$ to $C_{12}$ alkoxyphenyl) amino group, a di ($C_1$ to $C_{12}$ alkylphenyl) amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl $C_1$ to $C_{12}$ alkylamino group, a $C_1$ to $C_{12}$ alkoxyphenyl $C_1$ to $C_{12}$ alkylamino group, a $C_1$ to $C_{12}$ alkylphenyl $C_1$ to $C_{12}$ alkylamino group, a di($C_1$ to $C_{12}$ alkoxyphenyl $C_1$ to $C_{12}$ alkyl) amino group, a di($C_1$ to $C_{12}$ alkylphenyl $C_1$ to $C_{12}$ alkyl) amino group, a 1-naphthyl $C_1$ to $C_{12}$ alkylamino group and a 2-naphthyl $C_1$ to $C_{12}$ alkylamino group.

The substituted silyl group includes silyl groups substituted by one, two or three groups selected from the group consisting of an alkyl group, an aryl group, an arylalkyl group and a mono-valent heterocyclic group. The substituted silyl group has a carbon atom number of usually 1 to 60, preferably 3 to 48. The alkyl group, aryl group, arylalkyl group and mono-valent heterocyclic group optionally have a substituent. Examples of the substituted silyl group include a trimethylsilyl group, a triethylsilyl group, a tri-n-propylsilyl group, a triisopropylsilyl group, a dimethylisopropylsilyl group, a diethylisopropylsilyl group, a t-butyldimethylsilyl group, a n-pentyldimethylsilyl group, a n-hexyldimethylsilyl group, a n-heptyldimethylsilyl group, a n-octyldimethylsilyl group, a 2-ethylhexyldimethylsilyl group, a n-nonyldimethylsilyl group, a n-decyldimethylsilyl group, a 3,7-dimethyloctyldimethylsilyl group, a n-lauryldimethylsilyl group, a phenyl $C_1$ to $C_{12}$ alkylsilyl group, a $C_1$ to $C_{12}$ alkoxyphenyl $C_1$ to $C_{12}$ alkylsilyl group, a $C_1$ to $C_{12}$ alkylphenyl $C_1$ to $C_{12}$ alkylsilyl group, a 1-naphthyl $C_1$ to $C_{12}$ alkylsilyl group, a 2-naphthyl $C_1$ to $C_{12}$ alkylsilyl group, a phenyl $C_1$ to $C_{12}$ alkyldimethylsilyl group, a triphenylsilyl group, a tri-p-xylylsilyl group, a tribenzylsilyl group, a diphenylmethylsilyl group, a t-butyldiphenylsilyl group and a dimethylphenylsilyl group.

The acyl group has a carbon atom number of usually 2 to 20, preferably 2 to 18. Examples of the acyl group include an acetyl group, a propionyl group, a butyryl group, an isobutyryl group, a pivaloyl group, a benzoyl group, a trifluoroacetyl group and a pentafluorobenzoyl group.

The acyloxy group has a carbon atom number of usually 2 to 20, preferably 2 to 18. Examples of the acyloxy group include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The imine residue includes residues obtained by removing one hydrogen atom from imine compounds (namely, meaning organic compounds having —N=C— in the molecule. Examples thereof include aldimines, ketimines, and compounds obtained by substituting a hydrogen atom connected to a nitrogen atom in these compounds by an alkyl group or the like). The imine residue has a carbon atom number of usually 2 to 20, preferably 2 to 18. Examples of the imine residue include groups represented by the following structural formulae.

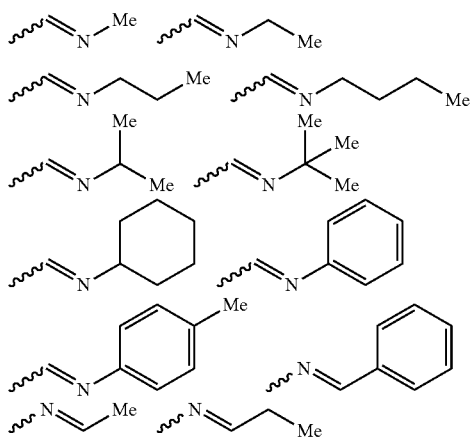

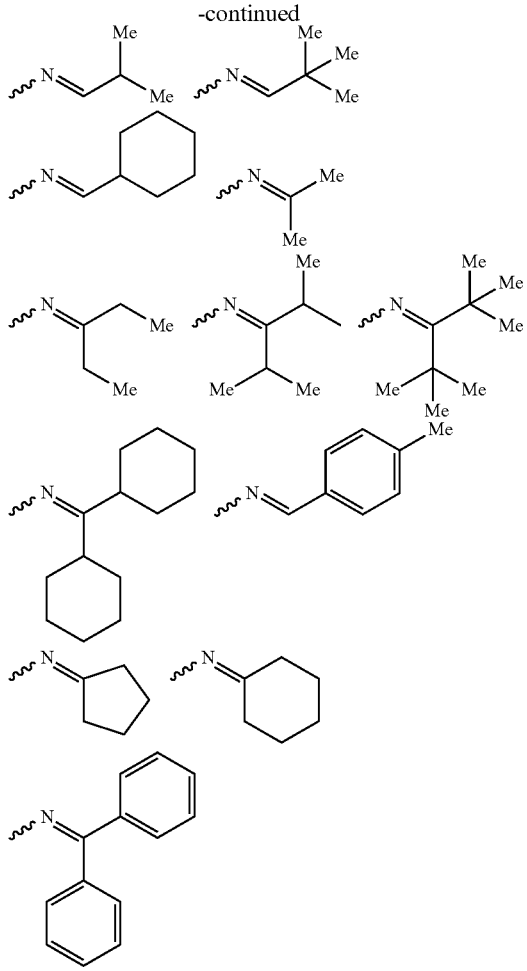

(wherein Me represents a methyl group, and the same shall apply hereinafter. The wavy line represents a connecting bond, and means a possibility of a geometric isomer such as a cis body, a trans body or the like depending on the kind of the imine residue.).

The amide group has a carbon atom number of usually 2 to 20, preferably 2 to 18. Examples of the amide group include a formamide group, an acetamide group, a propioamide group, a butyroamide group, a benzamide group, a trifluoroacetamide group, a pentafluorobenzamide group, a diformamide group, a diacetamide group, a dipropioamide group, a dibutyroamide group, a dibenzamide group, a ditrifluoroacetamide group and a dipentafluorobenzamide group.

The acid imide group includes residues obtained by removing from an acid imide one hydrogen atom connected to its nitrogen atom. The acid imide group has a carbon atom number of 4 to 20. Examples of the acid imide group include groups shown below.

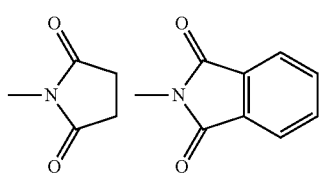

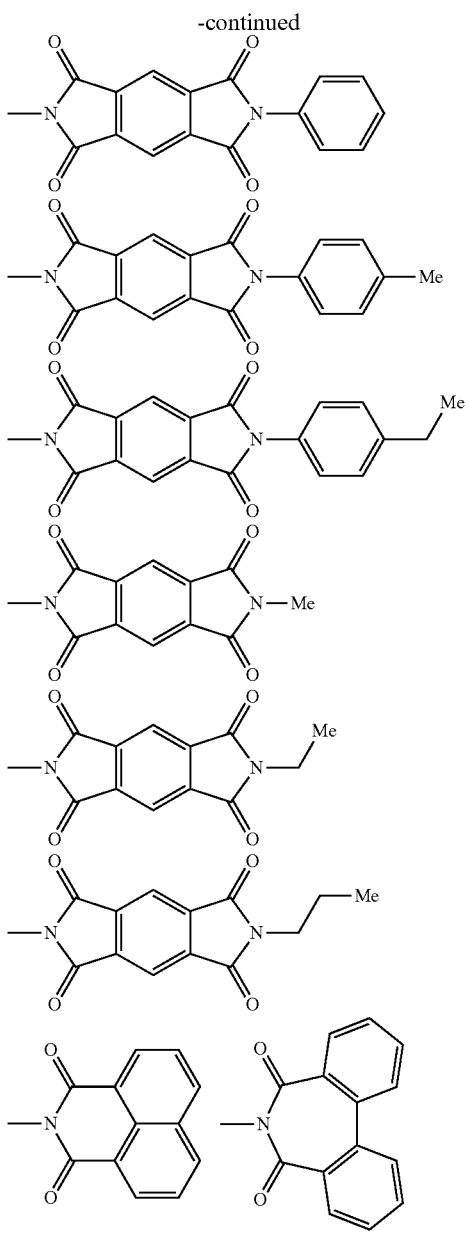

The substituted carboxyl group includes carboxyl groups substituted by an alkyl group, an alkenyl group, an alkynyl group, an aryl group, an arylalkyl group or a mono-valent heterocyclic group, and preferable are carboxyl groups substituted by an alkyl group, an aryl group, an arylalkyl group or a mono-valent heterocyclic group. The above-described alkyl group, alkenyl group, alkynyl group, aryl group, arylalkyl group or mono-valent heterocyclic group optionally has a substituent. The carbon atom number of the substituted carboxyl group is usually 2 to 60, preferably 2 to 48. The carbon atom number of the substituted carboxyl group does not include the carbon atom number of the substituent. Examples of the substituted carboxyl group include a methoxycarbonyl group, an ethoxycarbonyl group, a n-propoxycarbonyl group, an isopropoxycarbonyl group, a n-butoxycarbonyl group, an isobutoxycarbonyl group, a t-butoxycarbonyl group, a n-pentyloxycarbonyl group, a n-hexyloxycarbonyl group, a cyclohexyloxycarbonyl group, a n-heptyloxycarbonyl group, a n-octyloxycarbonyl group, a 2-ethylhexyloxycarbonyl group, a n-nonyloxycarbonyl group, a n-decyloxycarbonyl group, a 3,7-dimethyloctyloxycarbonyl group, a n-dodecyloxycarbonyl group, a trifluoromethoxycarbonyl group, a pentafluoroethoxycarbonyl group, a perfluorobutoxycarbonyl group, a perfluorohexyloxycarbonyl group, a perfluorooctyloxycarbonyl group, a phenoxycarbonyl group, a naphthoxycarbonyl group and a pyridyloxycarbonyl group.

In the formula (I), $X^1$ represents an oxygen atom, a sulfur atom or —N($R^N$)—.

$X^1$ in the formula (I) represents preferably a sulfur atom or —N($R^N$)—, more preferably a sulfur atom, for further improving electric field effect mobility in the case of use of the polymer compound of the present invention in an organic transistor.

In the formula (I), $R^1$ and $R^2$ represent preferably a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group or a mono-valent heterocyclic group, more preferably a hydrogen atom, an alkyl group or an aryl group, further preferably a hydrogen atom.

Further, from the standpoint of easiness of synthesis of a monomer, repeating units represented by the formula (II) are preferable among repeating units represented by the formula (I).

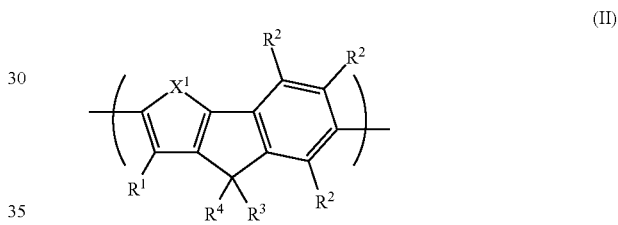

(II)

[wherein $R^1$, $R^2$, $R^3$, $R^4$ and $X^1$ represent the same meaning as described above.]

From the standpoint of easiness of synthesis of a monomer, $R^1$ and $R^2$ in the formula (II) represent, each independently, preferably a hydrogen atom, an alkyl group or an aryl group, more preferably a hydrogen atom.

From the standpoint of easiness of synthesis of a monomer, $R^3$ and $R^4$ in the formula (II) represent, each independently, preferably a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group or a mono-valent heterocyclic group, more preferably an alkyl group or an aryl group.

$X^1$ in the formula (II) represents preferably a sulfur atom or —N($R^N$)—, more preferably a sulfur atom, for further improving electric field effect mobility in the case of use of the polymer compound of the present invention in an organic transistor.

Examples of the repeating unit represented by the formula (II) include repeating units represented by the formulae (II-1) to (II-8).

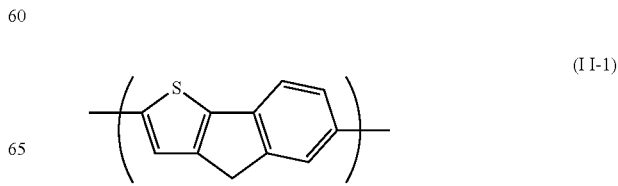

(II-1)

-continued

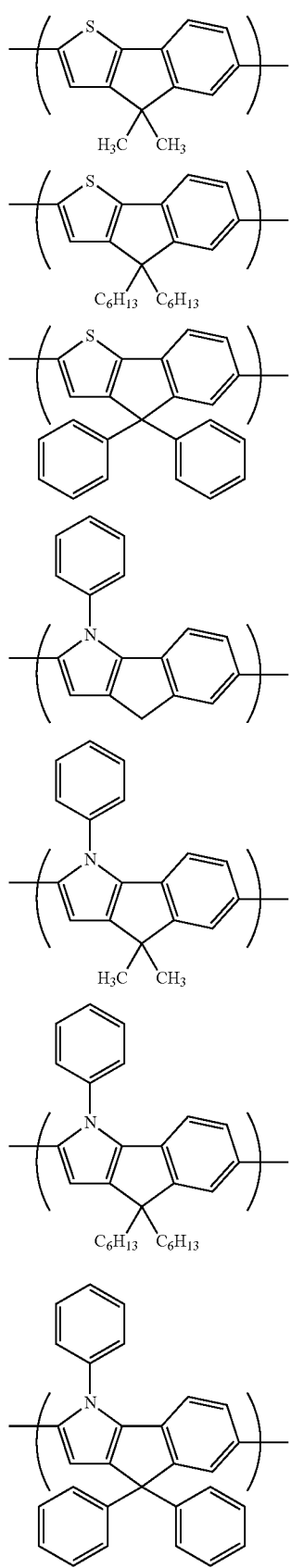

The content proportion of repeating units represented by the formula (I) is preferably 30 mol % or more and 100 mol % or less, more preferably 35 mol % or more and 95 mol % or less, further preferably 40 mol % or more and 90 mol % or less in all repeating units in the polymer compound of the present invention, for further improving electric field effect mobility in the case of use of the polymer compound of the present invention in an organic transistor.

It is preferable that the polymer compound of the present invention further contains a repeating unit represented by the formula (III), from the standpoint of solubility in a solvent.

$$—(Ar^1)— \qquad (III)$$

[wherein $Ar^1$ represents an arylene group, a di-valent heterocyclic group or a di-valent aromatic amine residue.].

The arylene group represented by $Ar^1$ means an atomic group obtained by removing two hydrogen atoms from an aromatic hydrocarbon, and includes also those having a condensed ring, and those having two or more independent benzene rings or condensed rings connected directly or via a group such as vinylene or the like. The arylene group optionally has a substituent. From the standpoint of easiness of synthesis, the substituent includes preferably an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a mono-valent heterocyclic group, a carboxyl group, a substituted carboxyl group, a cyano group and a nitro group, more preferably an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a mono-valent heterocyclic group, a carboxyl group, a substituted carboxyl group, a cyano group and a nitro group.

A portion of the arylene group excluding the substituent has a carbon atom number of usually 6 to 60, preferably 6 to 20. The total carbon atom number of the arylene group including the substituent is usually 6 to 100.

The arylene group includes a phenylene group (the following formulae 1 to 3), a naphthalenediyl group (the following formulae 4 to 13), an anthracene-diyl group (the following formulae 14 to 19), a biphenyl-diyl group (the following formulae 20 to 25), a terphenyl-diyl group (the following formulae 26 to 28), a fluorene-diyl group (the following formulae 29 to 31), a benzofluorene-diyl group (the following formulae 32 to 39), and a condensed ring compound group (the following formulae 40 to 53).

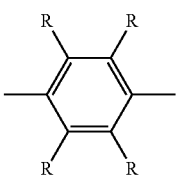

1

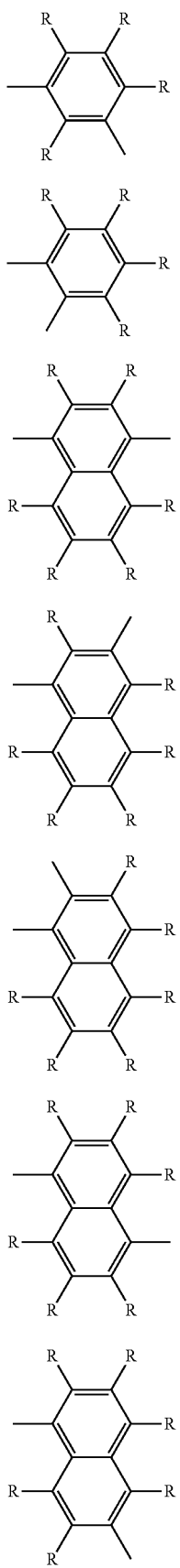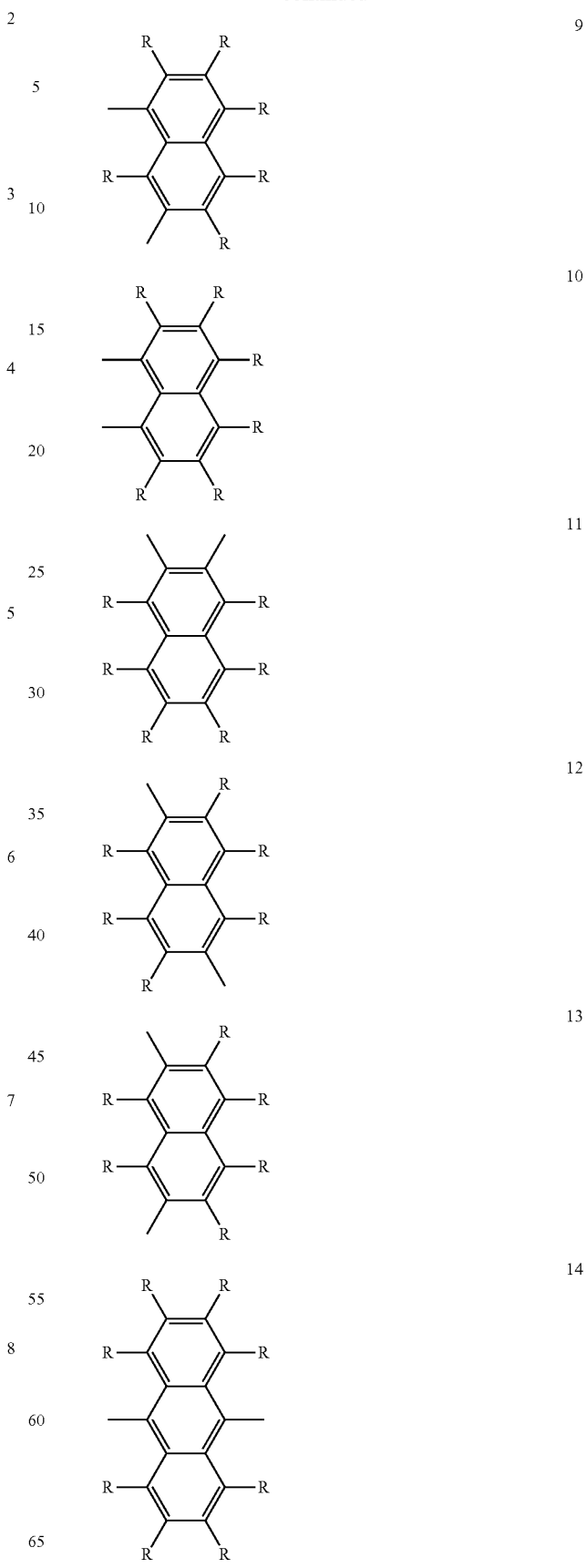

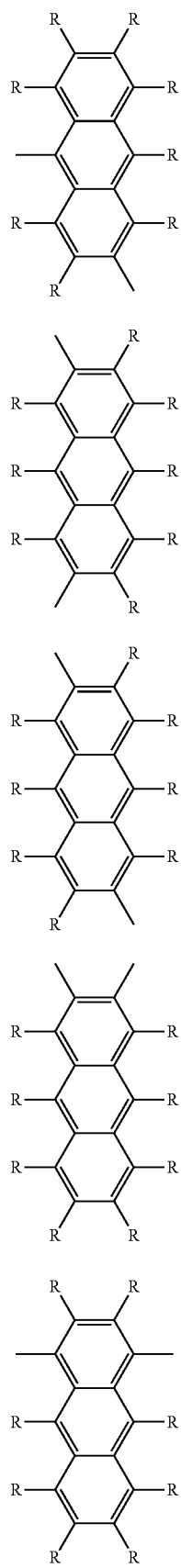
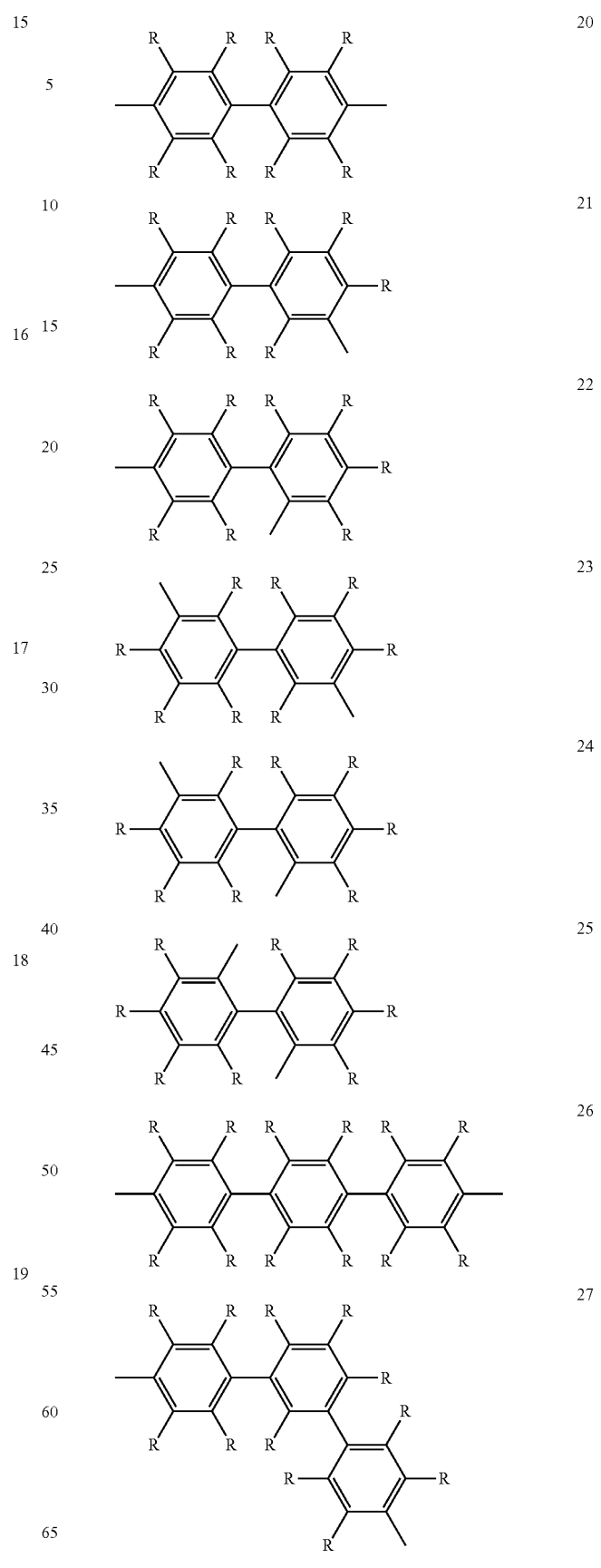

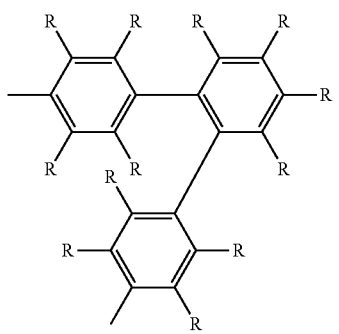
28
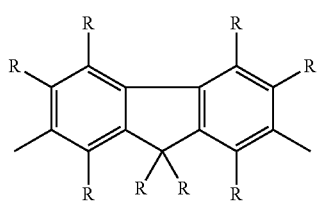
29
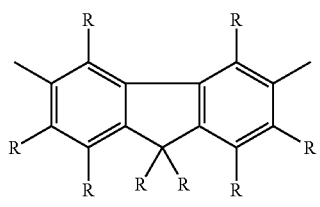
30
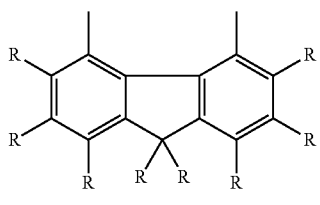
31
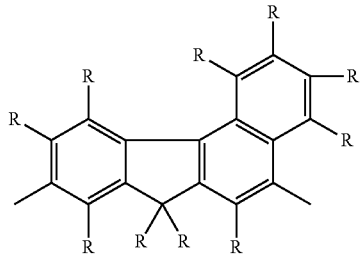
32
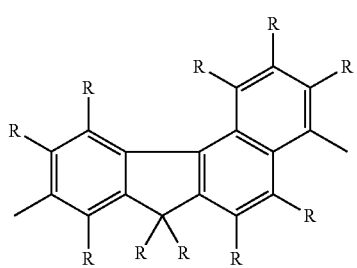
33
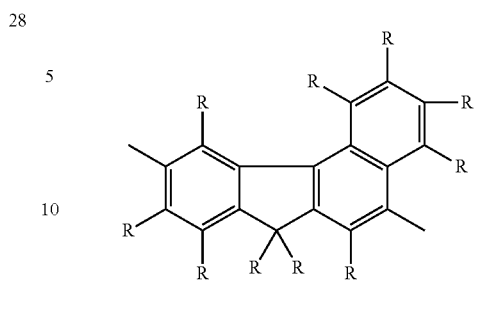
34
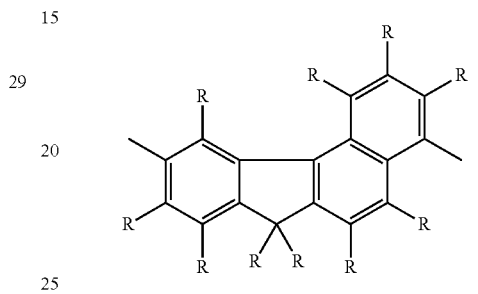
35
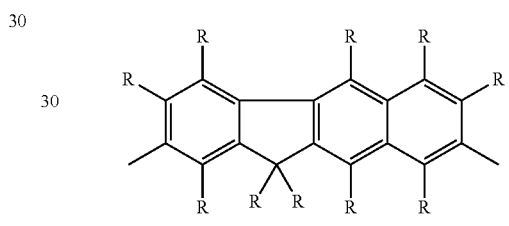
36
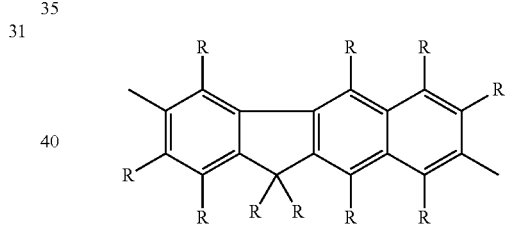
37
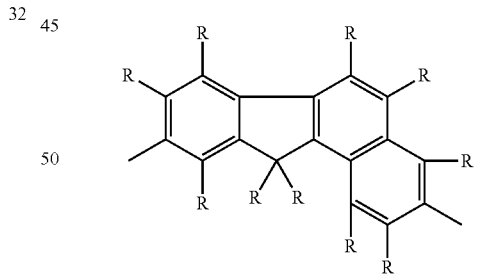
38
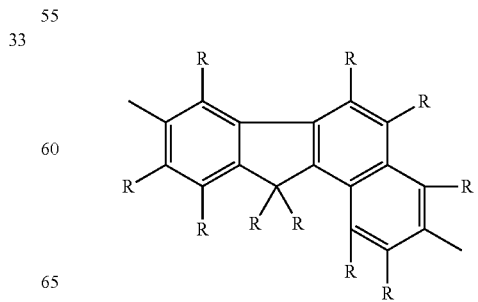
39

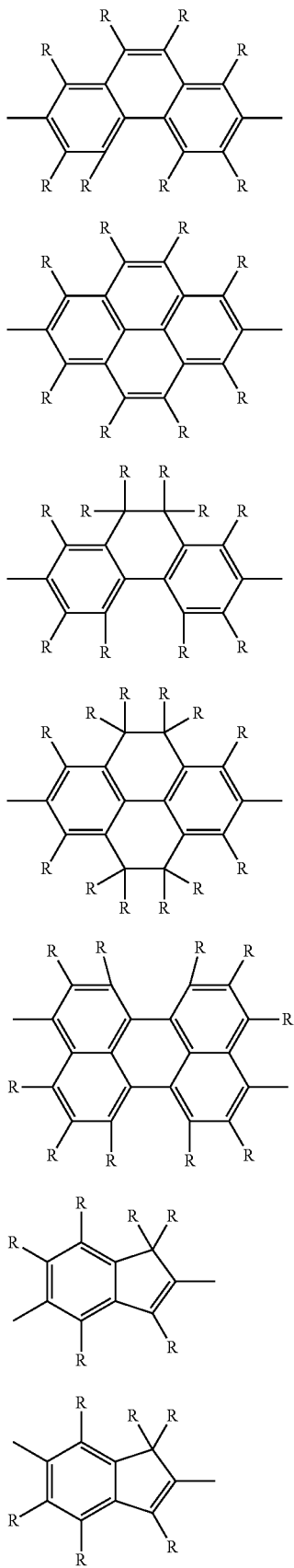
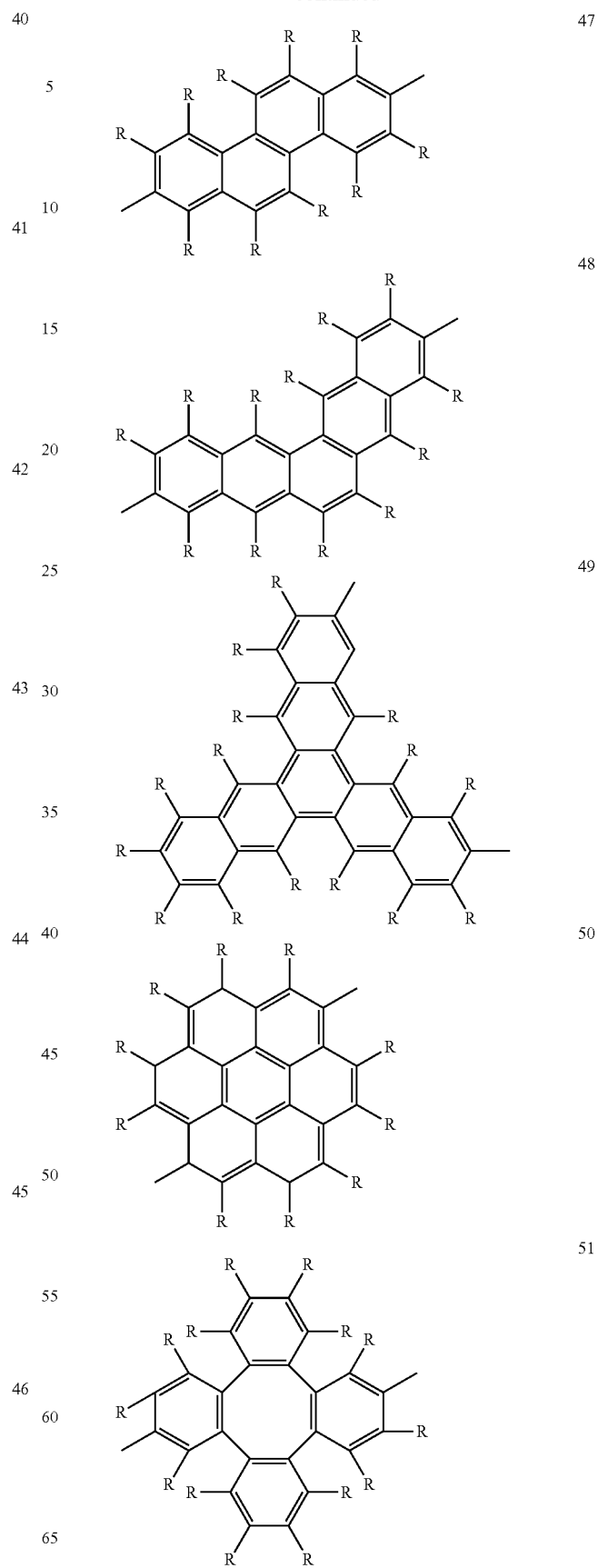

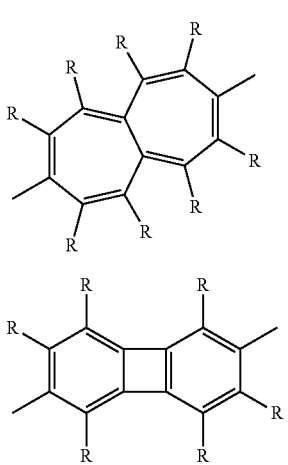

The di-valent heterocyclic group means an atomic group remaining after removal of two hydrogen atoms from a heterocyclic compound, and optionally has a substituent.

Here, the heterocyclic compound means an organic compound having a cyclic structure in which elements constituting the ring include not only a carbon atom, but also a hetero atom such as oxygen, sulfur, nitrogen, phosphorus, boron, arsenic and the like contained in the ring. Among di-valent heterocyclic groups, di-valent aromatic heterocyclic groups are preferable. The di-valent heterocyclic group optionally has a substituent. From the standpoint of easiness of synthesis, the substituent includes preferably an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a mono-valent heterocyclic group, a carboxyl group, a substituted carboxyl group, a cyano group and a nitro group, more preferably an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a mono-valent heterocyclic group, a carboxyl group, a substituted carboxyl group, a cyano group and a nitro group.

A portion of the di-valent heterocyclic group excluding the substituent has a carbon atom number of usually 3 to 60. The total carbon atom number of the di-valent heterocyclic group including the substituent is usually 3 to 100.

The di-valent heterocyclic group includes the following groups.

Di-valent heterocyclic groups containing a nitrogen atom as a hetero atom: a pyridinediyl group (the following formulae 101 to 106), a diazaphenylene group (the following formulae 107 to 110), a quinolinediyl group (the following formulae 111 to 125), a quinoxalinediyl group (the following formulae 126 to 130), an acridinediyl group (the following formulae 131 to 134), a bipyridyldiyl group (the following formulae 135 to 137), a phenanthrolinediyl group (the following formulae 138 to 140).

5-membered ring heterocyclic groups containing an oxygen atom, a silicon atom, a nitrogen atom, a sulfur atom, a selenium atom, a boron atom, a phosphorus atom or the like as a hetero atom (the following formulae 141 to 145).

5-membered ring condensed hetero groups containing an oxygen atom, a silicon atom, a nitrogen atom, a selenium atom or the like as a hetero atom (the following formulae 146 to 157).

5-membered ring heterocyclic groups containing an oxygen atom, a silicon atom, a nitrogen atom, a sulfur atom, a selenium atom or the like as a hetero atom, which are connected at an α-position of its hetero atom to form a dimer or an oligomer (the following formulae 158 to 159).

5-membered ring heterocyclic groups containing an oxygen atom, a silicon atom, a nitrogen atom, a sulfur atom, a selenium atom or the like as a hetero atom, which are connected at an α-position of its hetero atom to a phenyl group (the following formulae 160 to 166).

5-membered ring condensed heterocyclic groups containing an oxygen atom, a nitrogen atom, a sulfur atom, a selenium atom or the like as a hetero atom, and carrying thereon a substituent such as a phenyl group, a furyl group or a thienyl group (the following formulae 167 to 172).

Groups containing an oxygen atom, a silicon atom, a nitrogen atom, a sulfur atom, a selenium atom or the like as a hetero atom, and having a fluorene-like structure (the following formulae 173 to 202).

6-membered ring condensed hetero groups containing an oxygen atom, a silicon atom, a nitrogen atom, a sulfur atom, a selenium atom, a boron atom, a phosphorus atom or the like as a hetero atom (the following formulae 203 to 205).

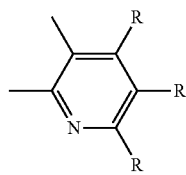

101

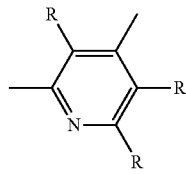

102

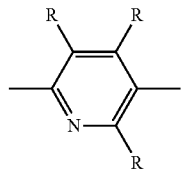

103

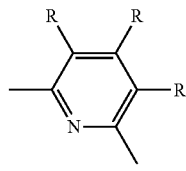

104

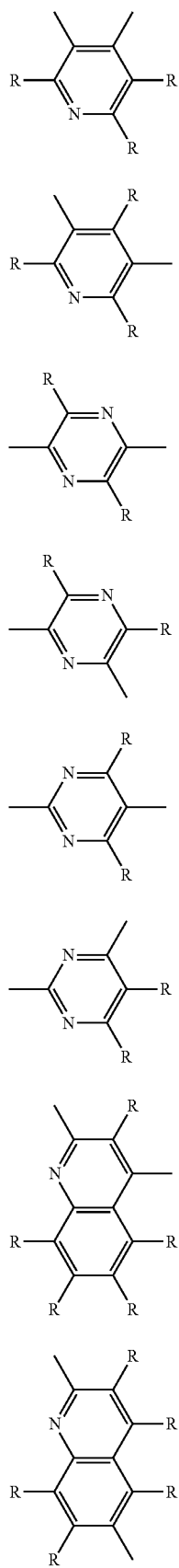
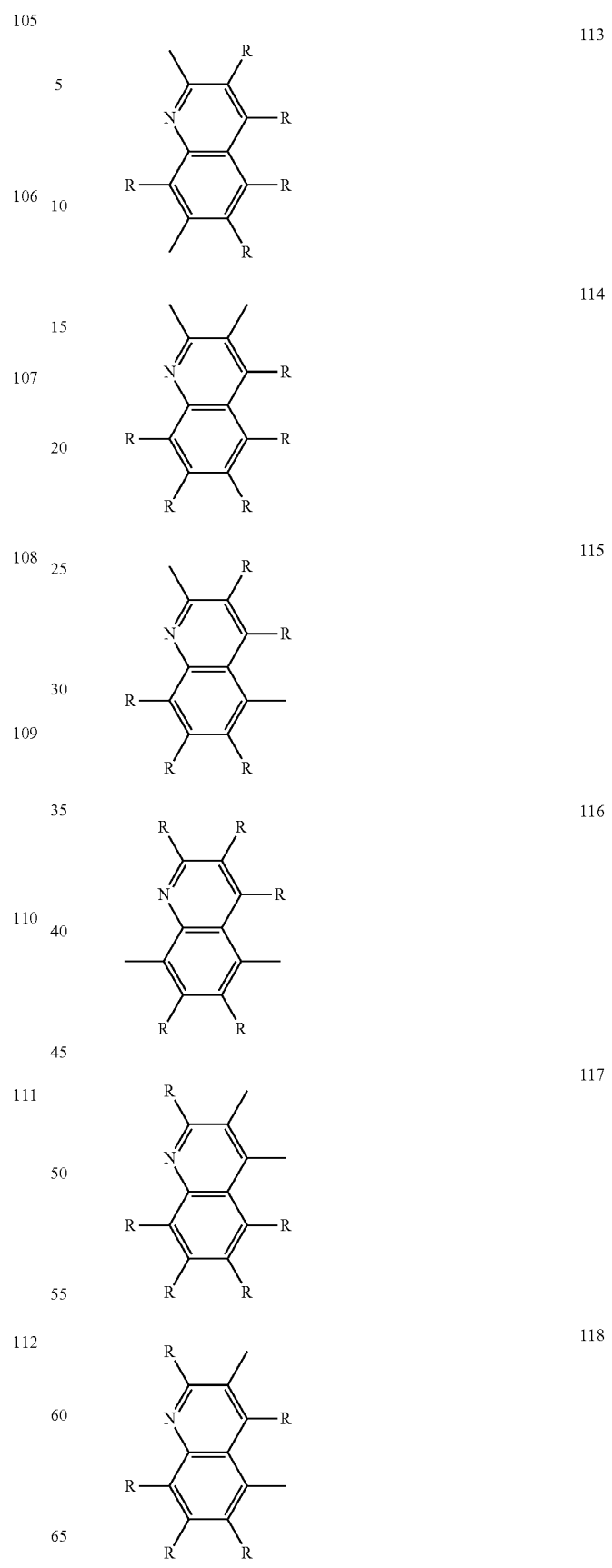

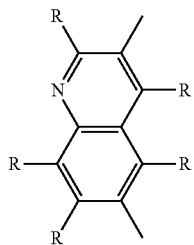
119
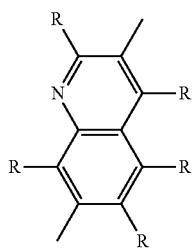
120
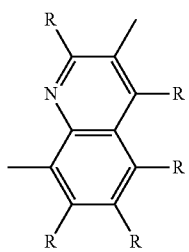
121
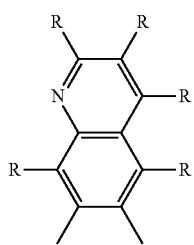
122
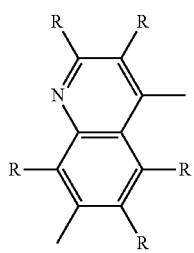
123
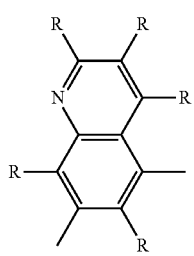
124
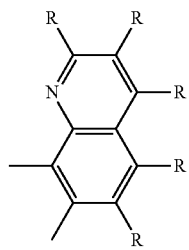
125
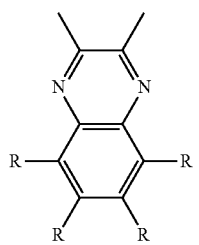
126
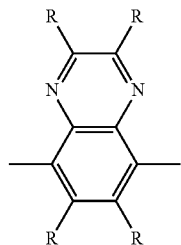
127
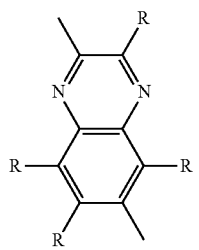
128
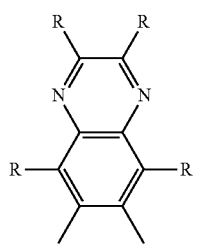
129
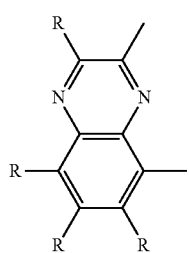
130

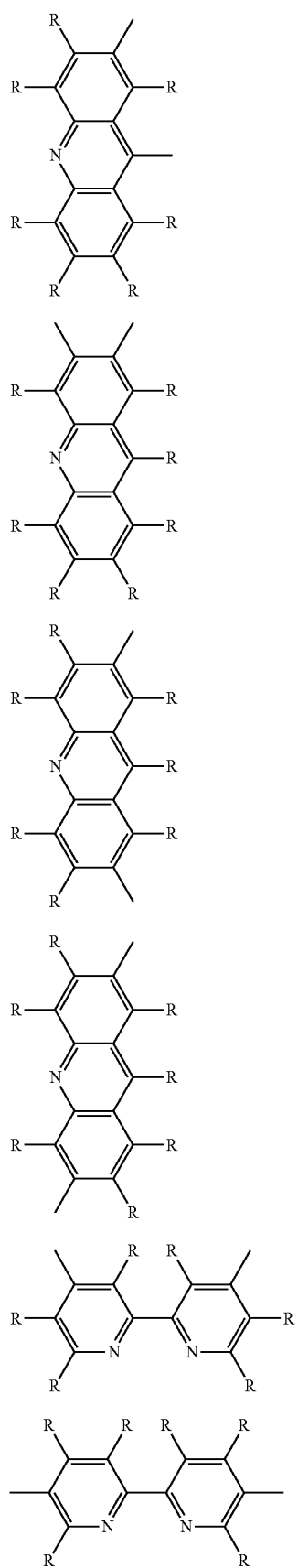
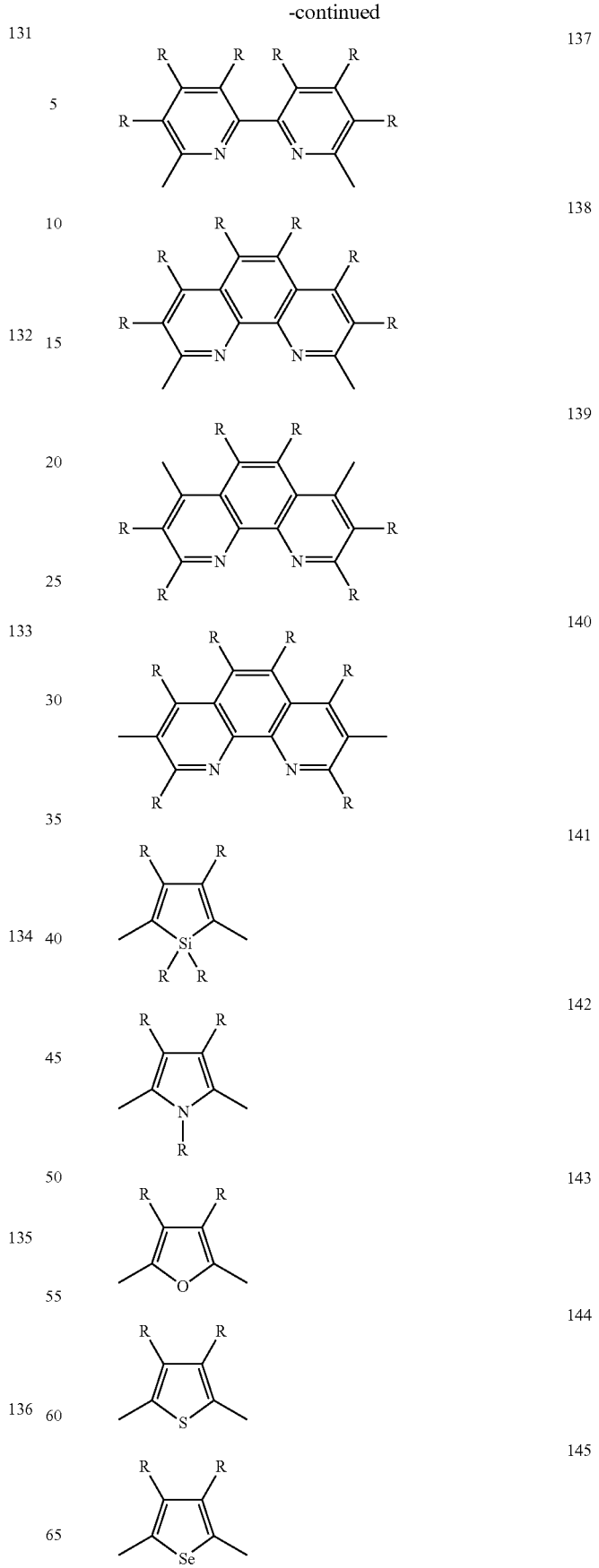

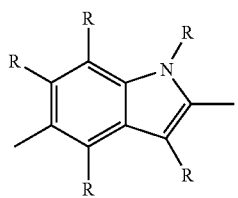
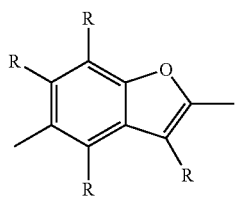
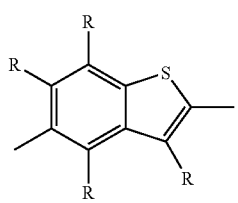
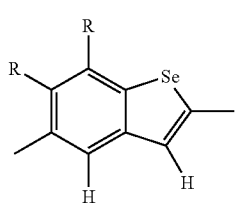
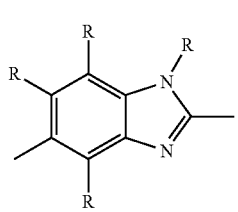
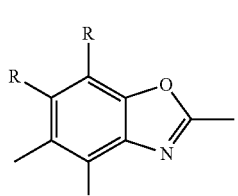
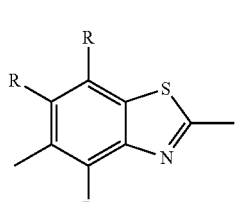
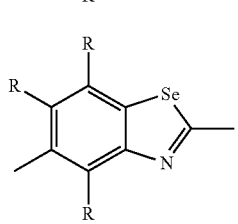
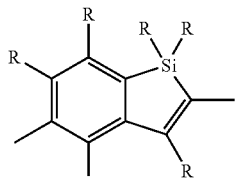
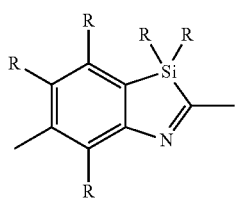
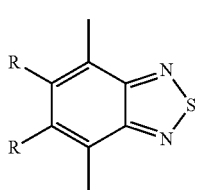
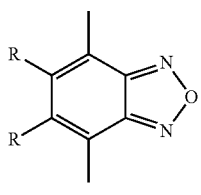
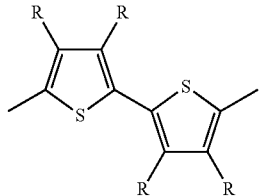
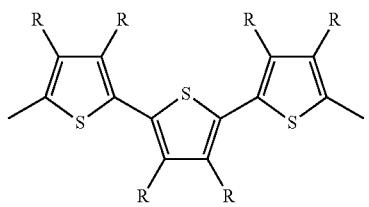
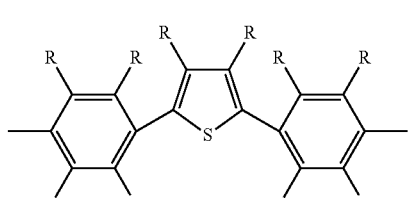
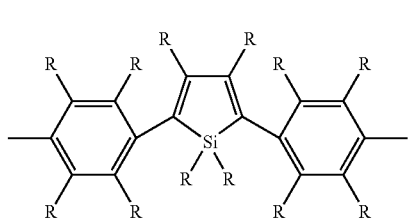

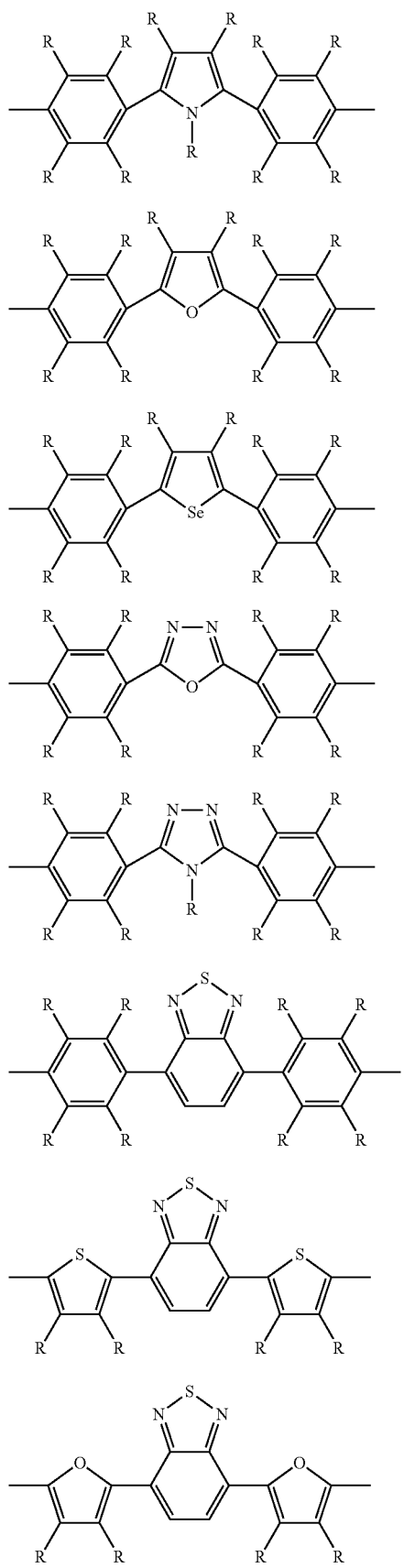
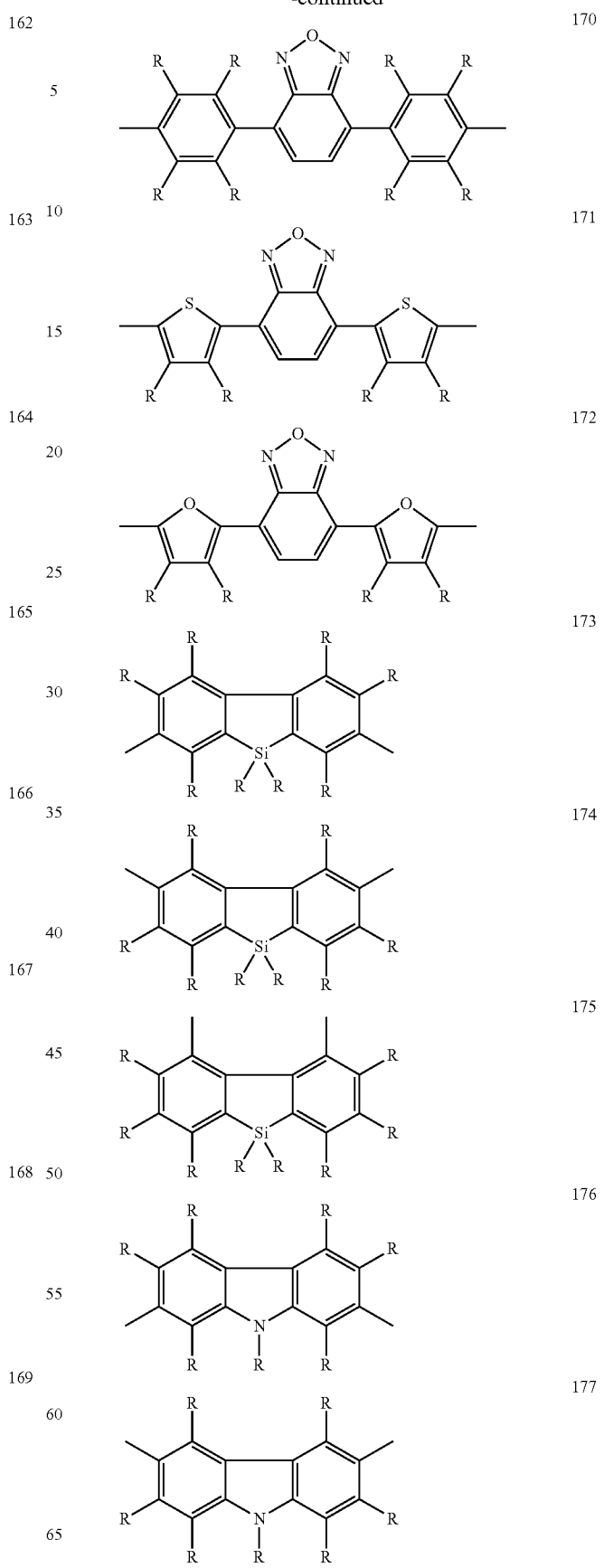

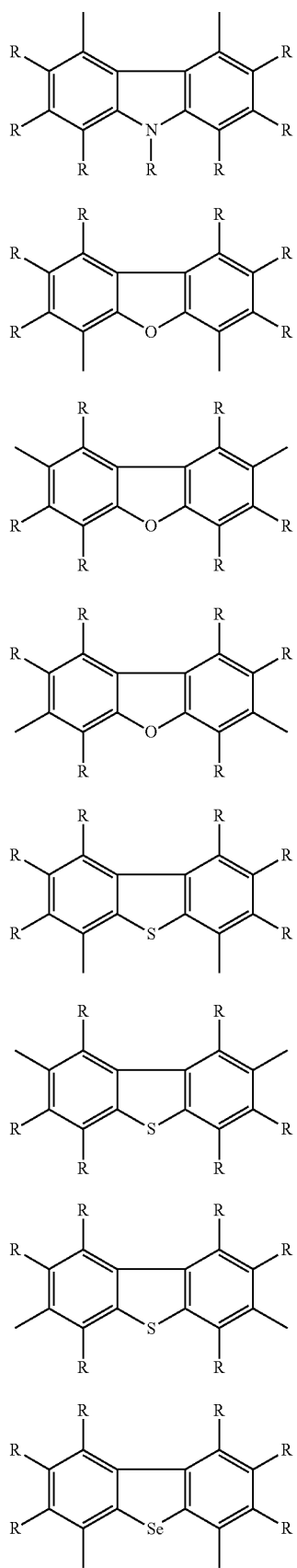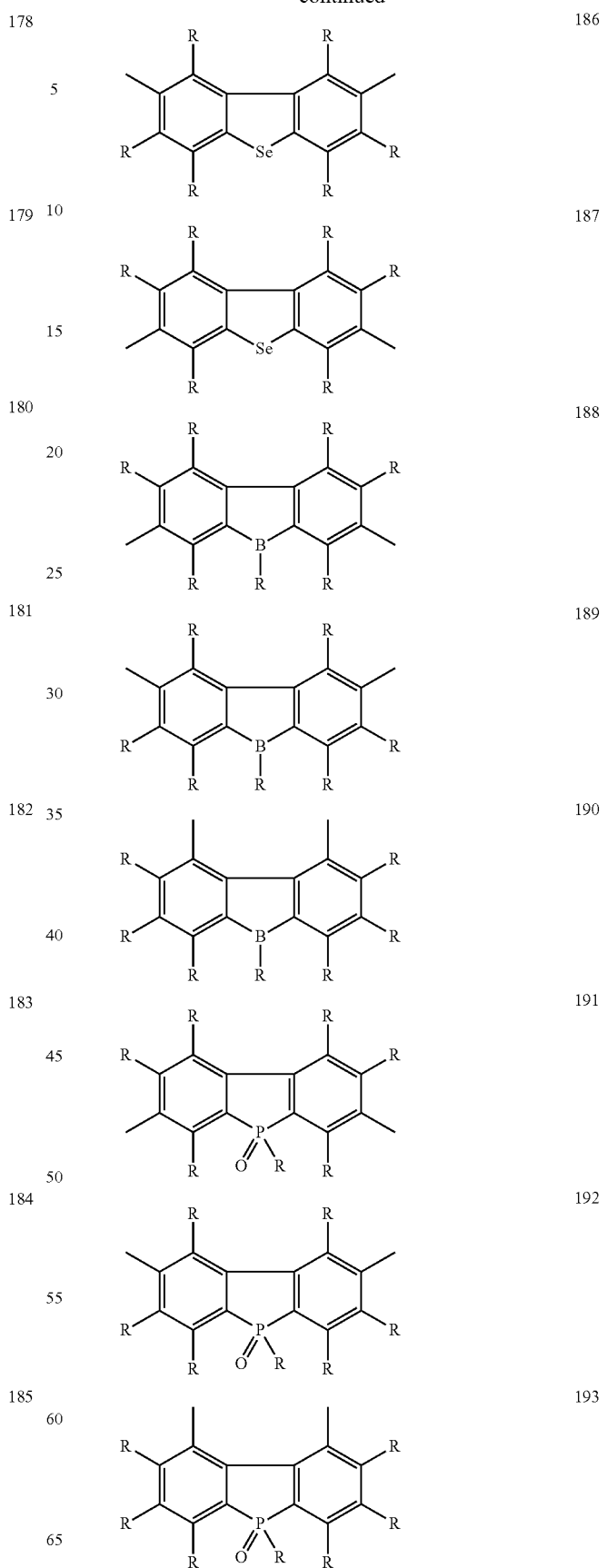

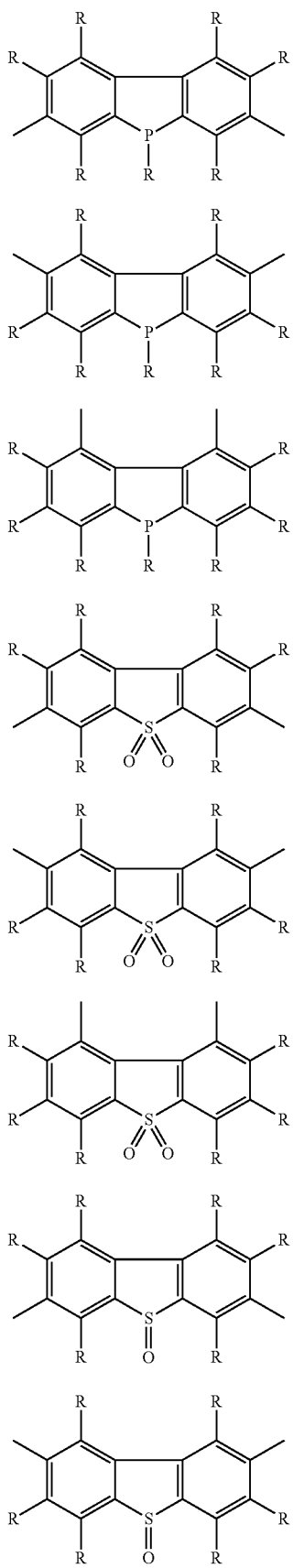

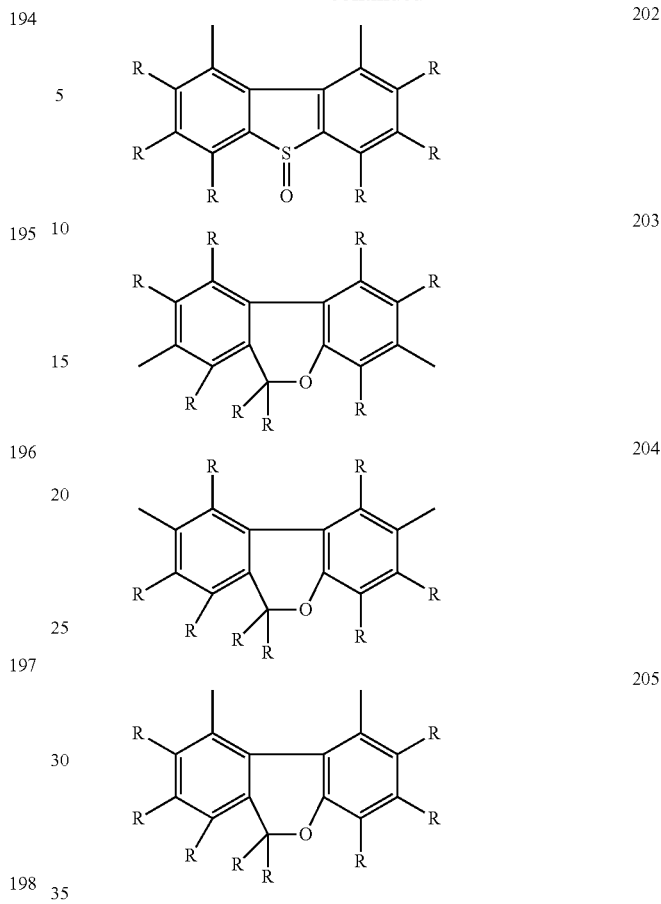

In the formulae 1 to 53 and 101 to 205, R represents a hydrogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a mono-valent heterocyclic group, a carboxyl group, a substituted carboxyl group, a cyano group or a nitro group, preferably a hydrogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, an amino group, a substituted amino group, a silyl group, a substituted silyl group, a halogen atom, an acyl group, an acyloxy group, an imine residue, an amide group, an acid imide group, a mono-valent heterocyclic group, a carboxyl group, a substituted carboxyl group, a cyano group or a nitro group. A plurality of Rs may be the same or mutually different.

The definitions, examples and the like of the alkyl group, alkenyl group, alkynyl group, alkoxy group, alkylthio group, aryl group, aryloxy group, arylthio group, arylalkyl group, arylalkoxy group, arylalkylthio group, arylalkenyl group, arylalkynyl group, substituted amino group, substituted silyl group, halogen atom, acyl group, acyloxy group, imine residue, amide group, acid imide group, mono-valent heterocyclic group and substituted carboxyl group are the same as the definitions, examples and the like of them represented by $R^1$, $R^2$ and $R^N$.

The di-valent aromatic amine residue includes groups represented by the formula (III-1).

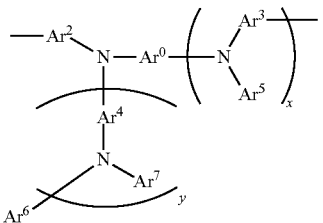
(III-1)

[wherein Ar⁰, Ar², Ar³ and Ar⁴ represent each independently an arylene group or a di-valent heterocyclic group, Ar⁵, Ar⁶ and Ar⁷ represent each independently an aryl group or a mono-valent heterocyclic group, and x and y represent each independently an integer of 0 to 5. A carbon atom in Ar² and a carbon atom in Ar⁰ may be connected directly, or connected via an oxygen atom or a sulfur atom, to form a ring. When there exist a plurality of Ar³s, Ar⁴s, Ar⁵s and Ar⁷s, these may be the same or mutually different.].

In the formula (III-1), x represents preferably an integer of 0 to 3, more preferably 0 or 1. y represents preferably an integer of 0 to 3, more preferably 0 or 1.

Examples of the group represented by the formula (III-1) include groups represented by the formulae (III-1-1) to (III-1-18).

(III-1-1)
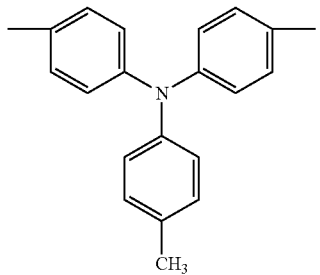

(III-1-2)
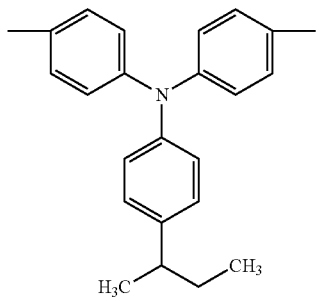

(III-1-3)
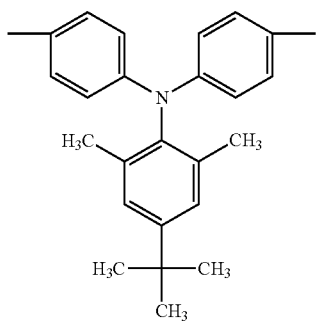

(III-1-4)
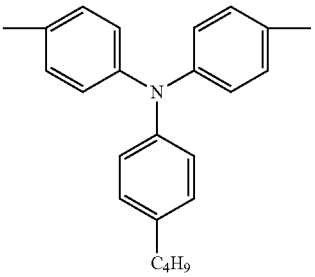

(III-1-5)
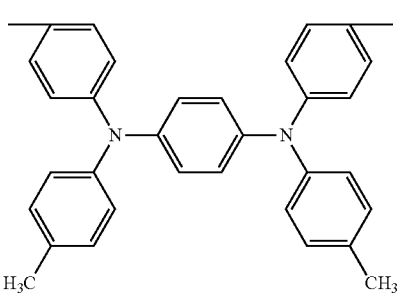

(III-1-6)
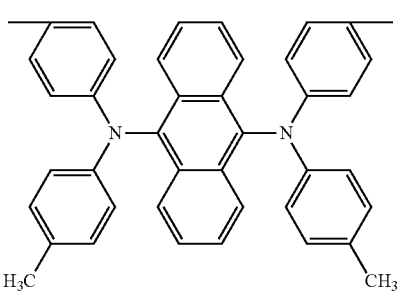

(III-1-7)
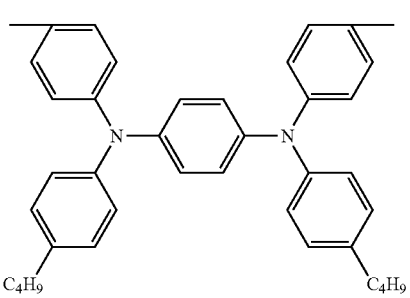

(III-1-8)
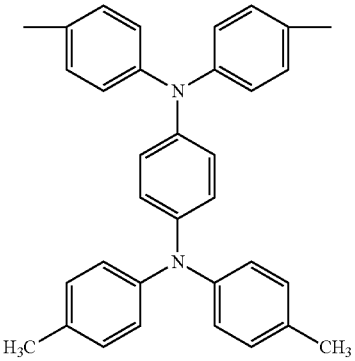

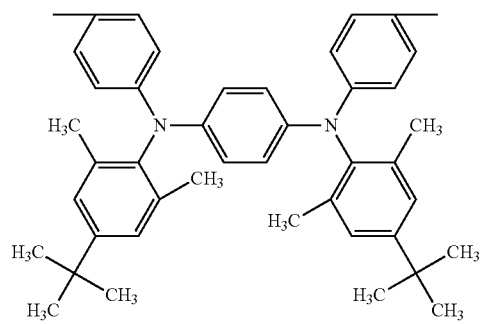 (III-1-9)
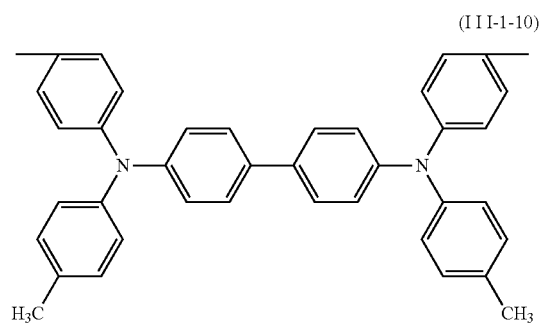 (III-1-10)
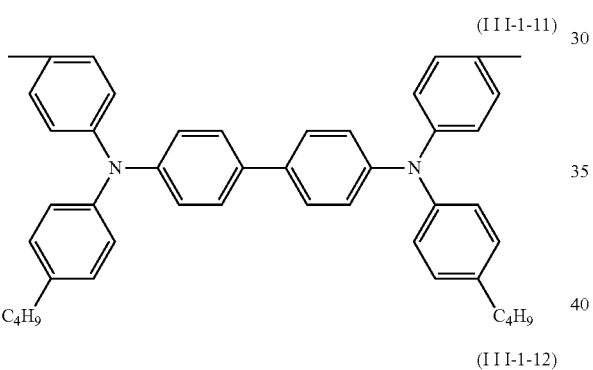 (III-1-11)
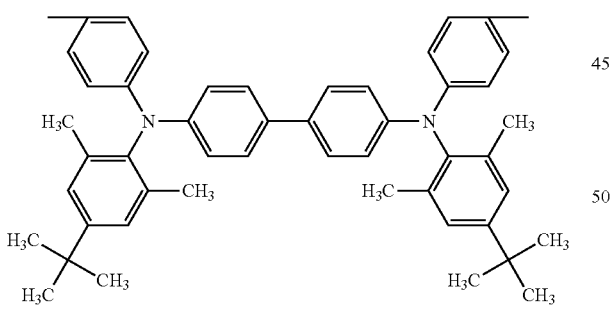 (III-1-12)
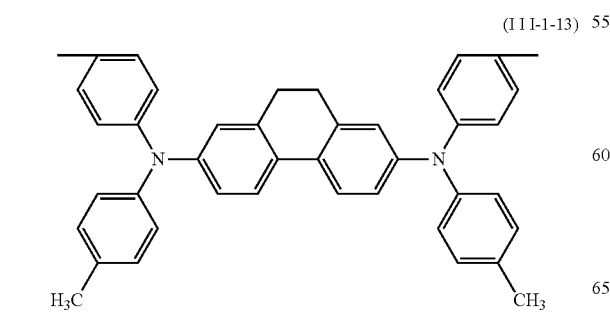 (III-1-13)
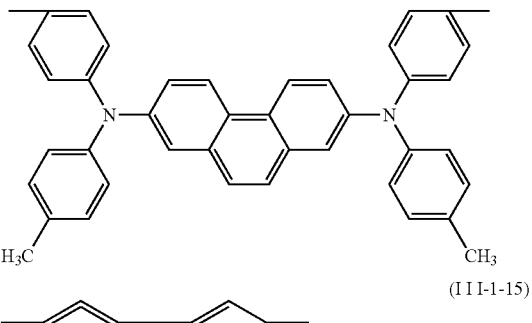 (III-1-14)
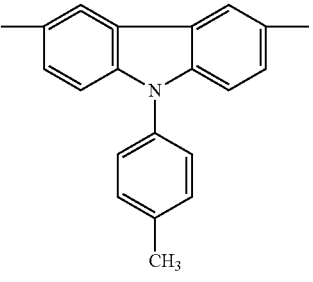 (III-1-15)
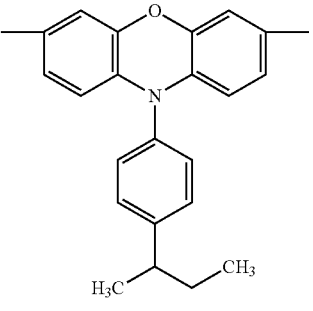 (III-1-16)
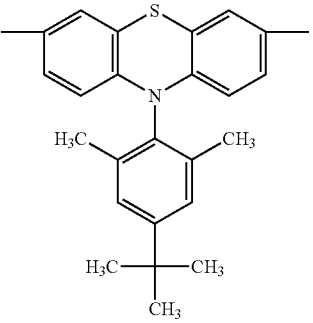 (III-1-17)
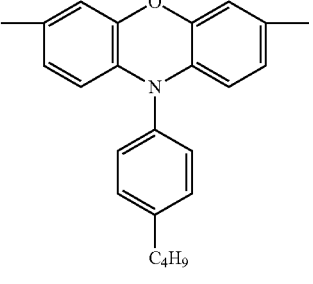 (III-1-18)
From the standpoint of easiness of synthesis of a raw material monomer, the arylene group represented by $Ar^1$ in the formula (III) is preferably a group represented by the formula (IV).

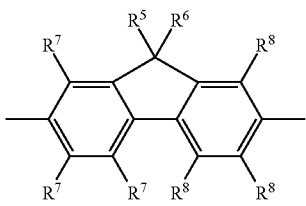

(IV)

[wherein $R^5$ and $R^6$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group, $R^7$ and $R^8$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group, and a plurality of $R^7$s may be the same or mutually different and a plurality of $R^8$s may be the same or mutually different.].

In the formula (IV), $R^5$ and $R^6$ represent preferably a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group, and from the standpoint of easiness of synthesis of a raw material monomer, represent preferably an aryl group or an alkyl group.

In the formula (IV), $R^7$ and $R^8$ represent preferably a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group, and from the standpoint of easiness of synthesis of a raw material monomer, represent preferably a hydrogen atom.

Examples of the group represented by the formula (IV) include groups represented by the formulae (IV-1) to (IV-12), preferably groups represented by the formulae (IV-1) to (IV-8).

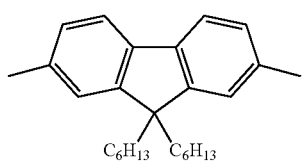

(IV-1)

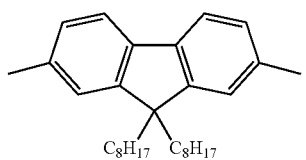

(IV-2)

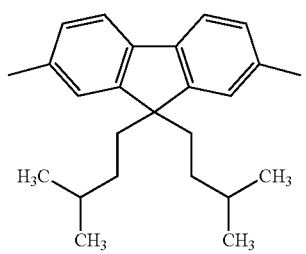

(IV-3)

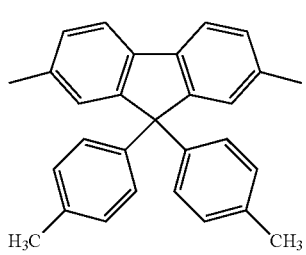

(IV-4)

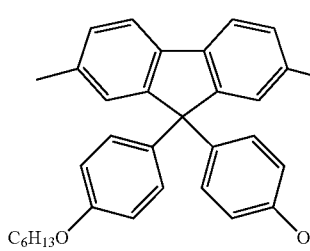

(IV-5)

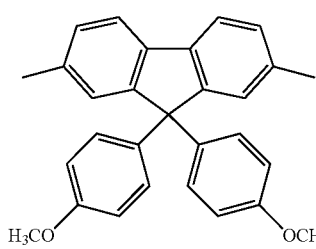

(IV-6)

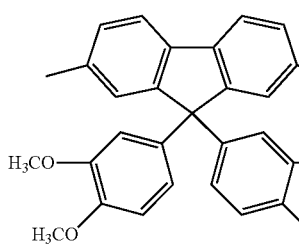

(IV-7)

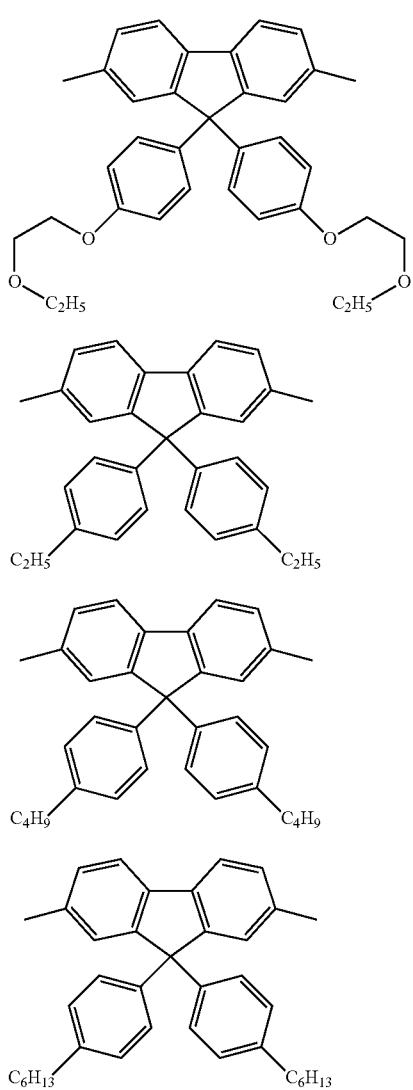
(IV-8)
(IV-9)
(IV-10)
(IV-11)

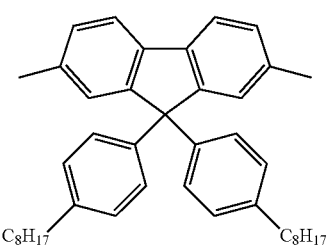
(IV-12)

The polymer compound of the present invention has a polystyrene-equivalent number average molecular weight of preferably $1\times10^3$ to $1\times10^8$, more preferably $1\times10^3$ to $1\times10^7$, further preferably $1\times10^4$ to $1\times10^7$, for further improving electric field effect mobility in the case of use thereof in an organic transistor. The polymer compound of the present invention has a polystyrene-equivalent weight average molecular weight of preferably $1\times10^3$ to $1\times10^8$, more preferably $1\times10^3$ to $1\times10^7$.

The polymer compound of the present invention may be a homopolymer or a copolymer. When the polymer compound of the present invention is a copolymer, the copolymer may be an alternative copolymer, a random copolymer, a block copolymer or a graft copolymer, or may be a polymer having an intermediate structure thereof, for example, a random copolymer having a block property. For obtaining a polymer compound having high fluorescent or phosphorescent quantum yield, random copolymers having a block property and block copolymers or graft copolymers are more preferable than complete random copolymers. The polymer compound of the present invention includes also a polymer compound having branching in the main chain and thus having three or more end parts, and a dendrimer.

Examples of the polymer compound of the present invention include polymer compounds represented by the formulae (P-11) to (P-25).

(P-11)
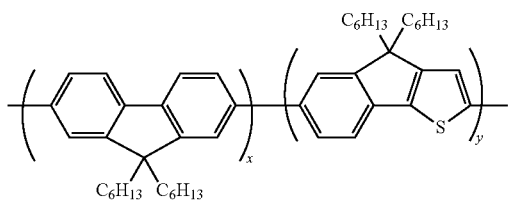

(P-12)
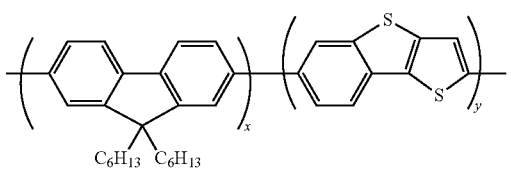

(P-13)
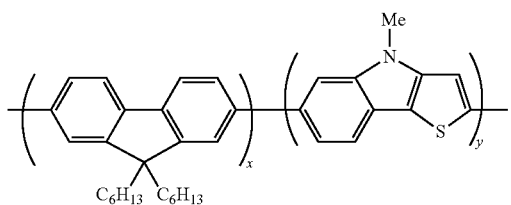

(P-14)
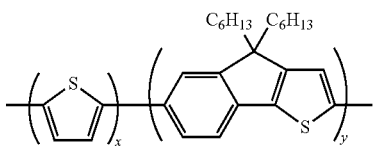

-continued
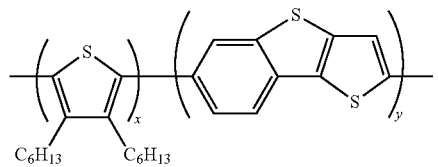
(P-15)
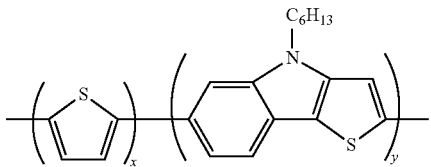
(P-16)
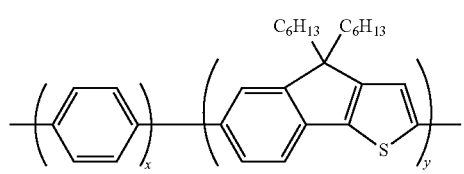
(P-17)
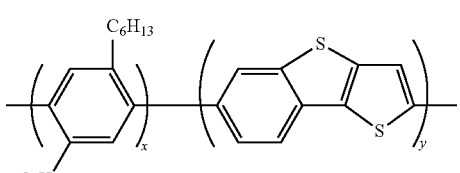
(P-18)
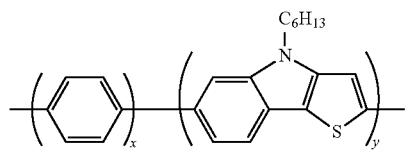
(P-19)
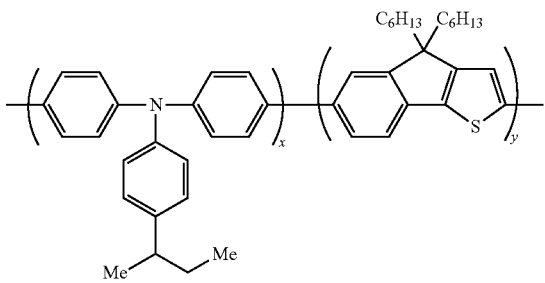
(P-20)
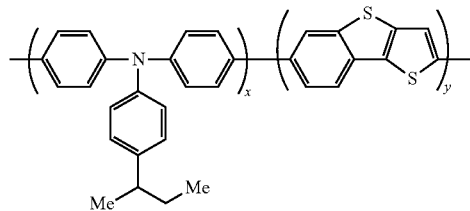
(P-21)
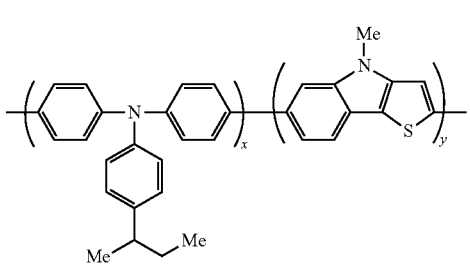
(P-22)
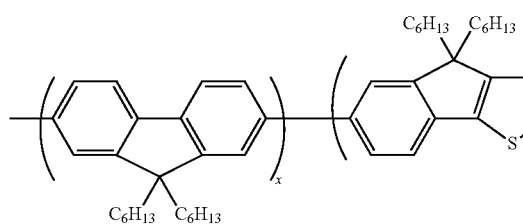
(P-23)
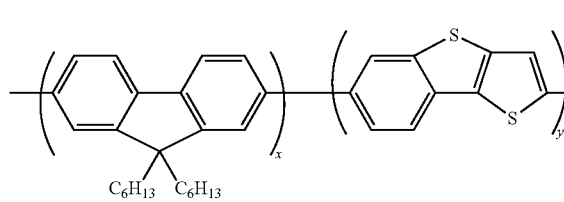
(P-24)

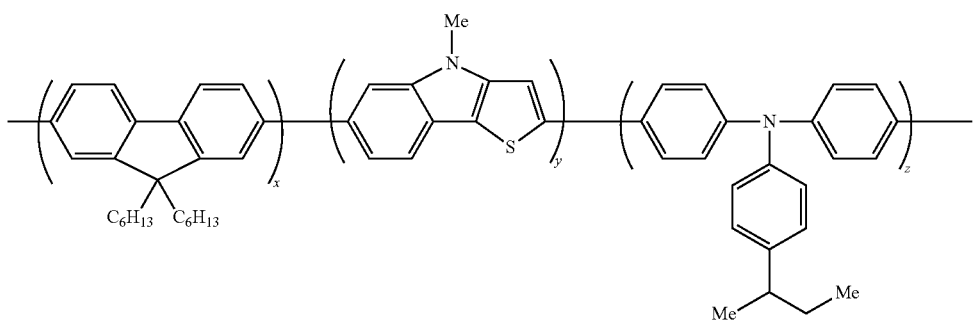

(P-25)

In the formulae (P-11) to (P-22), x and y are numbers representing composition ratios (molar ratios) of repeating units, providing that x+y=100. x represents usually 0 to 70, preferably 5 to 65, more preferably 20 to 60. y represents usually 30 to 100, preferably 35 to 95, more preferably 40 to 80.

In the formulae (P-23) to (P-25), x, y and z are numbers representing composition ratios (molar ratios) of repeating units, providing that x+y+z=100. x represents usually 5 to 80, preferably 40 to 70. y represents usually 10 to 90, preferably 40 to 80. z represents usually 1 to 30, preferably 2 to 10.

As for the end group of the polymer compound of the present invention, if a polymerization active group remains intact, there is a possibility of reduction in the light emitting property and the life-time when fabricated into a device, thus, the end group may be protected with a stable group. As the end group, those having a conjugated bond continuing to a conjugated structure of the main chain are preferable, and for example, there are exemplified structures connecting to an aryl group or a mono-valent heterocyclic group via a carbon-carbon bond. Specifically, substituents described as Chemical Formula 10 in JP-A No. 9-45478 are exemplified.

As the good solvent for the polymer compound of the present invention, exemplified are chloroform, methylene chloride, dichloroethane, tetrahydrofuran, toluene, xylene, mesitylene, tetralin, decalin and n-butylbenzene. Depending on the structure and the molecular weight of the polymer compound, the polymer compound can be dissolved usually in an amount of 0.1 wt % or more in these solvents.

Next, the method of producing the polymer compound of the present invention will be explained.

The polymer compound of the present invention can be produced by using a compound represented by the formula (V) and a compound represented by $Y^1$-A-$Y^2$ as a raw material, and condensation-polymerizing them. -A- represents a repeating unit represented by the formula (I) or (II).

Examples of the compound represented by the formula (V) include compounds represented by the formulae (V-1) to (V-21).

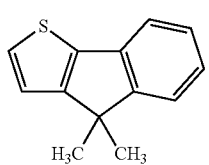

(V-1)

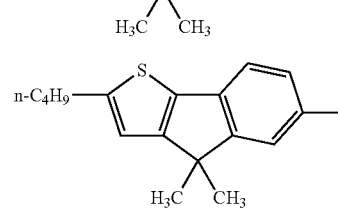

(V-2)

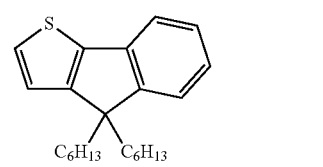

(V-3)

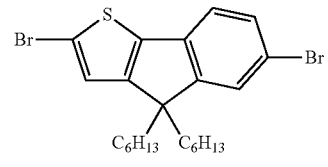

(V-4)

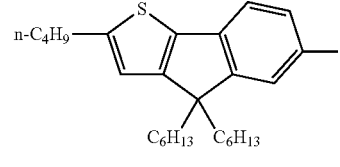

(V-5)

(V-6)

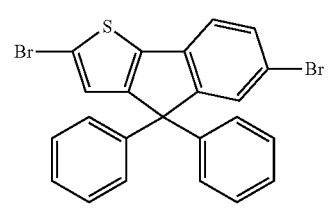

(V-7)

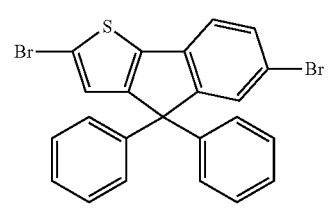

(V-8)

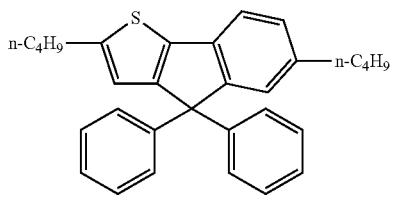 (V-9)

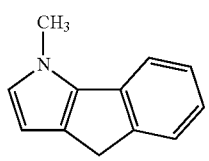 (V-10)

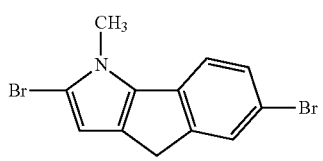 (V-11)

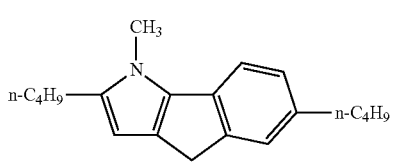 (V-12)

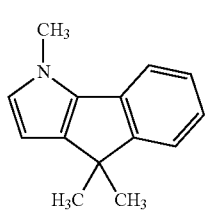 (V-13)

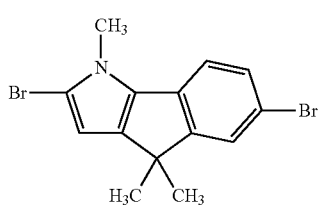 (V-14)

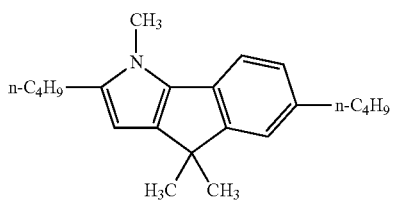 (V-15)

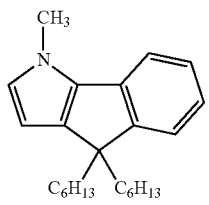 (V-16)

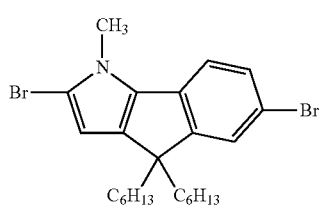 (V-17)

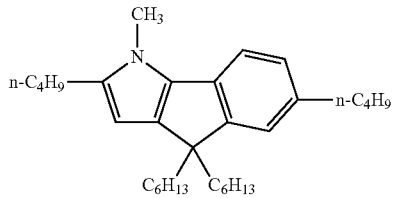 (V-18)

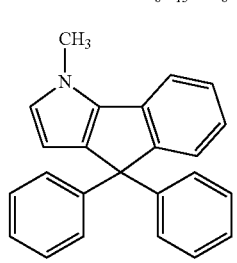 (V-19)

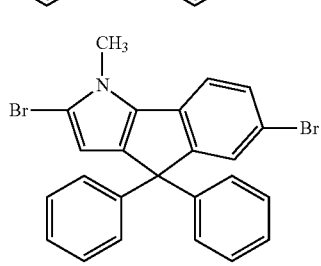 (V-20)

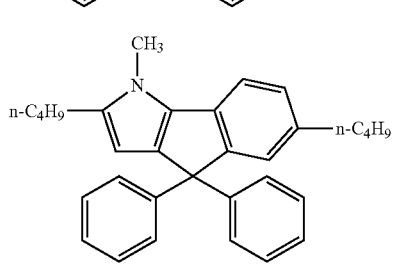 (V-21)

$Y^1$ and $Y^2$ represent each independently a group correlated with condensation polymerization.

In the production method of the present invention, the substituents ($Y_1$ and $Y_2$) correlated with condensation polymerization include a halogen atom, an alkyl sulfonate group, an aryl sulfonate group, an arylalkyl sulfonate group, a group derived from a borate, a sulfoniummethyl group, a phosphoniummethyl group, a phosphonate methyl group, a methyl monohalide group, —B(OH)$_2$, a formyl group, a cyano group and a vinyl group.

Here, the halogen atom includes a fluorine atom, a chlorine atom, a bromine atom and an iodine atom.

As the alkyl sulfonate group, a methane sulfonate group, an ethane sulfonate group and a trifluoromethane sulfonate group are exemplified.

As the aryl sulfonate group, a benzene sulfonate group and a p-toluene sulfonate group are exemplified.

As the arylalkyl sulfonate group, a benzyl sulfonate group is exemplified.

As the group derived from a borate, groups represented by the following formulae are exemplified.

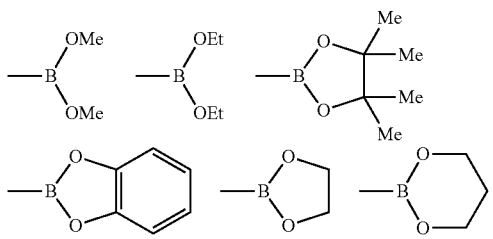

(wherein Et represents an ethyl group, and the same shall apply hereinafter.).

As the sulfoniummethyl group, groups represented by the following formulae are exemplified.

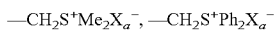

(wherein $X_a$ represents a halogen atom, and Ph represents a phenyl group.).

As the phosphoniummethyl group, groups represented by the following formula are exemplified.

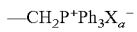

(wherein $X_a$ and Ph represent the same meaning as described above.).

As the phosphonate methyl group, groups represented by the following formula are exemplified.

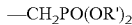

(wherein R' represents an alkyl group, an aryl group or an arylalkyl group.).

As the methyl monohalide group, a methyl fluoride group, a methyl chloride group, a methyl bromide group and a methyl iodide group are exemplified.

Preferable groups as the group correlated with condensation polymerization include a halogen atom, an alkyl sulfonate group, an aryl sulfonate group and an arylalkyl sulfonate group in the case of use of a 0-valent nickel complex such as, for example, in the Yamamoto coupling reaction and the like, though varying depending on the kind of the polymerization reaction. An alkyl sulfonate group, a halogen atom, a group derived from a borate, and —B(OH)₂ are mentioned in the case of use of a nickel catalyst or a palladium catalyst such as in the Suzuki coupling reaction and the like.

Production of the polymer compound of the present invention can be carried out, specifically, by dissolving a compound having several groups correlated with condensation polymerization as a monomer, if necessary, in an organic solvent, using, for example, an alkali and a suitable solvent, at a temperature of not lower than the melting point and not higher than the boiling point of the organic solvent. For production of the polymer compound of the present invention, there can be used known methods described in, for example, "Organic Reactions", Volume 14, page 270-490, John Wiley & Sons, Inc., 1965; "Organic Syntheses", Collective Volume VI, page 407-411, John Wiley & Sons, Inc., 1988; Chemical Review (Chem. Rev.), Volume 95, page 2457 (1995); Journal of Organometallic Chemistry (J. Organomet. Chem.), Volume 576, page 147 (1999); Macromolecular Chemistry Macromolecular Symposium (Makromol. Chem., Macromol. Symp.), Volume 12th, page 229 (1987).

In the method of producing the polymer compound of the present invention, known condensation reactions can be used, depending on the group correlated with condensation polymerization.

As the method of producing the polymer compound of the present invention, exemplified are a method of polymerization of the correspondent monomer by the Suzuki coupling reaction, a method of polymerization thereof by the Grignard reaction, a method of polymerization thereof with a Ni(0) complex, a method of polymerization thereof with an oxidizer such as FeCl₃ and the like, a method of electrochemical oxidation polymerization thereof, and a method by decomposition of an intermediate polymer having a suitable leaving group.

Of them, a method of polymerization by the Suzuki coupling reaction, a method of polymerization by the Grignard reaction and a method of polymerization with a nickel 0-valent complex are preferable from the standpoint of easiness of control of the structure.

Among the production methods of the polymer compound of the present invention, preferable are production methods in which the groups correlated with condensation polymerization ($Y_1$ and $Y_2$) are each independently selected from the group consisting of halogen atoms, alkyl sulfonate groups, aryl sulfonate groups and arylalkyl sulfonate groups, and condensation polymerization is carried out in the present of a nickel 0-valent complex.

The raw material compounds to be used in production of the polymer compound of the present invention include dihalogenated compounds, bis(alkyl sulfonate) compounds, bis (aryl sulfonate) compounds, bis(arylalkyl sulfonate) compounds, halogen-alkyl sulfonate compounds, halogen-aryl sulfonate compounds, halogen-arylalkyl sulfonate compounds, alkyl sulfonate-aryl sulfonate compounds, alkyl sulfonate-arylalkyl sulfonate compounds, and aryl sulfonate-arylalkyl sulfonate compounds.

In this case, there is mentioned a method in which a polymer compound having a controlled sequence is produced by using, for example, a halogen-alkyl sulfonate compound, a halogen-aryl sulfonate compound, a halogen-arylalkyl sulfonate compound, an alkyl sulfonate-aryl sulfonate compound, an alkyl sulfonate-arylalkyl sulfonate compound, or an aryl sulfonate-arylalkyl sulfonate compound as the raw material compound.

Among the production methods of the polymer compound of the present invention, preferable is a production method in which the groups correlated with condensation polymerization ($Y_1$ and $Y_2$) are selected each independently from halogen atoms, alkyl sulfonate groups, aryl sulfonate groups, arylalkyl sulfonate groups, —B(OH)₂ and borates, and the ratio of the sum (J) of mole numbers of halogen atoms, alkyl sulfonate groups, aryl sulfonate groups and arylalkyl sulfonate groups to the sum (K) of mole numbers of groups derived from —B(OH)₂ and borates, in all raw material compounds, is substantially 1 (usually, K/J is in the range of 0.7 to 1.2), and condensation polymerization is carried out using a nickel catalyst or palladium catalyst.

As combinations of raw material compounds, there are mentioned combinations of a dihalogenated compound, a bis(alkyl sulfonate) compound, a bis(aryl sulfonate) compound or a bis(arylalkyl sufonate) compound with a diboric acid compound or a diborate compound.

Other raw material compounds include a halogen-boric acid compound, a halogen-borate compound, an alkyl sulfonate-boric acid compound, an alkyl sulfonate-borate compound, an aryl sulfonate-boric acid compound, an aryl sulfonate-borate compound, an arylalkyl sulfonate-boric acid compound, an arylalkyl sulfonate-boric acid compound and an aryl alkyl sulfonate-borate compound.

A polymer compound having a controlled sequence can be produced by using a halogen-boric acid compound, a halogen-borate compound, an alkyl sulfonate-boric acid compound, an alkyl sulfonate-borate compound, an aryl sulfonate-boric acid compound, an aryl sulfonate-borate compound, an arylalkyl sulfonate-boric acid compound, an arylalkyl sulfonate-borate compound or an arylalkyl sulfonate-borate compound, as the raw material compound.

In the production method of the polymer compound of the present invention, it is preferable that the solvent to be used is subjected to a sufficient deoxygenation treatment and the reaction is progressed under an inert atmosphere, for in general suppressing side reactions, though varying depending on the reaction and compounds to be used. Further, it is preferable to perform a dehydration treatment likewise. However, this is not applicable to the case of a reaction in a two-phase system with water such as in the Suzuki coupling reaction, and the like.

Exemplified as the solvent are saturated hydrocarbons such as pentane, hexane, heptane, octane, cyclohexane and the like, unsaturated hydrocarbons such as benzene, toluene, ethylbenzene, xylene and the like, halogenated saturated hydrocarbons such as carbon tetrachloride, chloroform, dichloromethane, chlorobutane, bromobutane, chloropentane, bromopentane, chlorohexane, bromohexane, chlorocyclohexane, bromocyclohexane and the like, halogenated unsaturated hydrocarbons such as chlorobenzene, dichlorobenzene, trichlorobenzene and the like, alcohols such as methanol, ethanol, propanol, isopropanol, butanol, t-butyl alcohol and the like, carboxylic acids such as formic acid, acetic acid, propionic acid and the like, ethers such as dimethyl ether, diethyl ether, methyl t-butyl ether, tetrahydrofuran, tetrahydropyran, dioxane and the like, amines such as trimethylamine, triethylamine, N,N,N',N'-tetramethylethylenediamine, pyridine and the like, amides such as N,N-dimethylformamide, N,N-dimethylacetamide, N,N-diethylacetamide, N-methylmorpholine oxide, and the like. These solvents may be used singly or in admixture. Of them, ethers are preferable, and tetrahydrofuran and diethyl ether are further preferable, as the solvent.

For progressing the reaction, an alkali or a suitable catalyst may be appropriately used. These may be advantageously selected depending on the reaction to be used. As the alkali or catalyst, those which are sufficiently dissolved in the solvent used in the reaction are preferable. As the method of applying an alkali or a catalyst, there is exemplified a method in which a solution of an alkali or a catalyst is added slowly to a reaction solution under an inert atmosphere such as argon, nitrogen and the like while stirring the solution, or reversely, the reaction solution is slowly added to a solution of an alkali or a catalyst.

When the polymer compound of the present invention is used in a polymer light emitting device and the like, the purity of the polymer compound exerts an influence on the device performances such as a light emitting property and the like, thus, it is preferable to purify the monomer before polymerization by a method such as distillation, sublimation purification, re-crystallization and the like, then, to polymerize the monomer. Further, it is preferable, after polymerization, to carry out a purification treatment such as re-precipitation purification, chromatographic fractionation and the like.

The compound of the present invention is represented by the formula (V). In the formula, $X^1$ represents an oxygen atom, a sulfur atom or $-N(R^N)-$, and $R^1$, $R^2$ and $R^N$ represent each independently a hydrogen atom, a halogen atom, an alkyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a cyano group or a nitro group. $R^9$ and $R^{10}$ represent each independently a hydrogen atom, a halogen atom, an alkyl group, an alkoxy group, an alkylthio group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a cyano group or a nitro group. A plurality of $R^2$s may be the same or mutually different.

The definitions, examples and the like of the alkyl group, alkoxy group, alkylthio group, aryl group, aryloxy group, arylthio group, arylalkyl group, arylalkoxy group, arylalkylthio group, arylalkenyl group, arylalkynyl group, amino group, substituted amino group, silyl group, substituted silyl group, halogen atom, acyl group, acyloxy group, imine residue, amide group, acid imide group, mono-valent heterocyclic group and substituted carboxyl group are the same as the definitions, examples and the like of them represented by $R^1$, $R^2$ and $R^N$.

From the standpoint of easiness of synthesis of a compound, $R^9$ and $R^{10}$ in the formula (V) represent preferably a hydrogen atom, an alkyl group, an alkoxy group, an alkylthio group, an aryloxy group, an arylthio group, an arylalkyl group, an arylalkoxy group, an arylalkylthio group, an arylalkenyl group, an arylalkynyl group or a mono-valent heterocyclic group, more preferably an alkyl group.

The production method of the present invention has a first step of reacting a compound represented by the formula (M-1-1a)

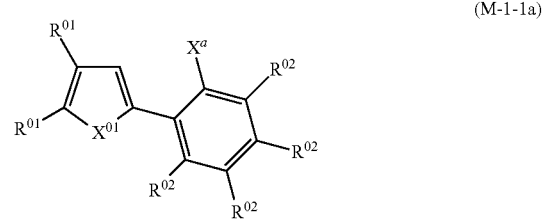

(M-1-1a)

[wherein $X^{01}$, $R^{01}$, $R^{02}$ and $X^a$ represent the same meaning as described above.]

with a compound represented by the formula (M-1-1b)

$R^{11}-C(=O)-R^{12}$ (M-1-1b)

[wherein $R^{11}$ and $R^{12}$ represent the same meaning as described above.]

preferably in the presence of a compound represented by $R^M$-M (wherein $R^M$ represents an alkyl group, an aryl group, an arylalkyl group, an alkenyl group or an alkynyl group, and M represents lithium or magnesium halide (for example, MgCl, MgBr, MgI)), to produce a compound represented by the formula (M-1-2a)

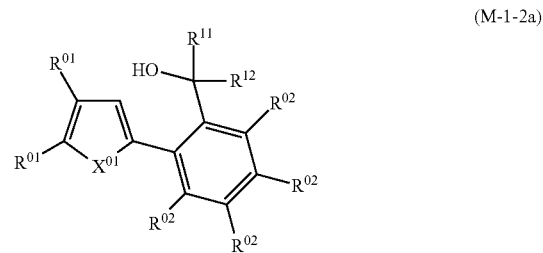

(M-1-2a)

[wherein $X^{01}$, $R^{01}$, $R^{02}$, $R^{11}$ and $R^{12}$ represent the same meaning as described above.].

The compound represented by $R^M$-M includes methyllithium, n-butyllithium, sec-butyllithium, tert-butyllithium, phenyllithium, n-hexylmagnesium bromide, and the like.

Specific embodiments include an embodiment in which a compound represented by the formula (M-1-1a) is reacted with a compound represented by $R^M$-M, then, reacted with a compound represented by the formula (M-1-1b).

In the reaction of the first step, a solvent is usually used, and examples of the solvent include saturated hydrocarbons such as pentane, hexane, heptane, octane, cyclohexane and the like; unsaturated hydrocarbons such as benzene, toluene, ethylbenzene, xylene and the like; ethers such as dimethyl ether, diethyl ether, methyl t-butyl ether, tetrahydrofuran, tetrahydropyran, dioxane and the like; etc. These solvents can be used singly or in combination of two or more.

The reaction temperature in the first step is approximately −100° C. to the boiling point of the solvent, preferably −80° C. to room temperature.

The production method of the present invention has a second step of subjecting the compound represented by the formula (M-1-2a) to a dehydration reaction to produce a compound represented by the formula (M-1-3a).

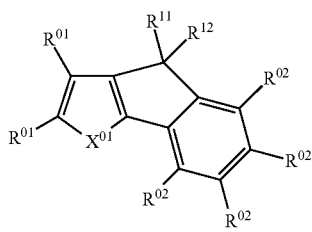

(M-1-3a)

[wherein $X^{01}$, $R^{01}$, $R^{02}$, $R^{11}$ and $R^{12}$ represent the same meaning as described above.].

The alkyl group, alkenyl group, alkynyl group, alkoxy group, alkylthio group, aryl group, aryloxy group, arylthio group, arylalkyl group, arylalkoxy group, arylalkylthio group, arylalkenyl group, arylalkynyl group, mono-valent heterocyclic group, heterocyclic thio group, substituted amino group, substituted silyl group, imine residue and acid imide group represented by $R^{01}$, $R^{02}$ and $R^{NN}$ in the formula (M-1-1a), the formula (M-1-2a) and the formula (M-1-3a) represent the same meaning as that of groups exemplified in the section of $R^1$, $R^2$ and $R^N$.

The halogen atom, alkyl group, alkoxy group, alkylthio group, aryl group, aryloxy group, arylthio group, arylalkyl group, arylalkoxy group, arylalkylthio group, arylalkenyl group, arylalkynyl group, mono-valent heterocyclic group, heterocyclic thio group, substituted amino group, substituted silyl group, acyl group, imine residue, amide group, acid imide group and substituted carboxyl group represented by $R^{11}$ and $R^{12}$ in the formula (M-1-2a) and the formula (M-1-3a) represent the same meaning as described above.

The second step is carried out preferably in the presence of an acid. The acid includes protonic acids, Lewis acids and the like. The protonic acid includes sulfonic acids such as methanesulfonic acid, trifluoromethanesulfonic acid, p-toluenesulfonic acid and the like; carboxylic acids such as formic acid, acetic acid, trifluoroacetic acid, propionic acid and the like; mineral acids such as sulfuric acid, hydrochloric acid, nitric acid, phosphoric acid and the like; etc. Of these protonic acids, strong mineral acids such as hydrochloric acid, sulfuric acid, nitric acid and the like are preferable. The Lewis acid includes halogenated boron compounds such as boron tribromide, boron trichloride, boron trifluoride ether complex and the like; halogenated metals such as aluminum chloride, titanium chloride, manganese chloride, iron chloride, cobalt chloride, copper chloride, zinc chloride, aluminum bromide, titanium bromide, manganese bromide, iron bromide, cobalt bromide, copper bromide, zinc bromide and the like; etc. Of these Lewis acids, a boron trifluoride ether complex is preferable. These acids (protonic acids, Lewis acids) can be used singly or in combination of two or more.

As the reaction medium in the second step, the above-described acids may be used, however, solvents other than them may also be used. The solvent to be used includes saturated hydrocarbons such as pentane, hexane, heptane, octane, cyclohexane and the like; halogenated saturated hydrocarbons such as carbon tetrachloride, chloroform, dichloroform, chlorobutane, bromobutane, chloropentane, bromopentane, chlorohexane, bromohexane, chlorocyclohexane, bromocyclohexane and the like; halogenated unsaturated hydrocarbons such as chlorobenzene, dichlorobenzene, trichlorobenzene and the like; nitrated compounds such as nitromethane, nitrobenzene and the like; etc. These solvents can be used singly or in combination of two or more.

The reaction temperature in the second step is approximately −50° C. to the boiling point of the solvent, preferably approximately 0° C. to the boiling point of the solvent.

The first step and the second step are preferably carried out under an atmosphere of an inert gas such as argon, nitrogen and the like.

The composition of the present invention is a composition containing the polymer compound of the present invention, and includes a composition containing at least one material selected from the group consisting of a hole transporting material, an electron transporting material and a light emitting material, and at least one polymer compound of the present invention, a composition containing at least two polymer compounds of the present invention, and the like.

The composition of the present invention may be a liquid composition, and is useful for fabrication of light emitting devices such as polymer light emitting devices, and organic transistors. The liquid composition contains the above-described polymer compound and a solvent. In this specification, "liquid composition" means a composition which is liquid in device fabrication, and usually, liquid at normal pressure (namely, 1 atm) and 25° C. The liquid composition is, in general, referred to as ink, ink composition, solution or the like in some cases.

The liquid composition of the present invention may also contain a low molecular weight light emitting material, a hole transporting material, an electron transporting material, a stabilizer, an additive for adjusting viscosity and/or surface tension, an antioxidant and the like, in addition to the above-described polymer compound. These optional components may be each used singly or in combination of two or more.

Examples of the low molecular weight light emitting material which may be contained in the liquid composition include naphthalene derivatives, anthracene, anthracene derivatives, perylene, perylene derivatives, polymethine dyes, xanthene dyes, coumarine dyes, cyanine dyes; metal complexes having a metal complex of 8-hydroxyquinoline as a ligand; metal complexes having a 8-hydroxyquinoline derivative as a ligand; other fluorescent metal complexes, aromatic amines, tetraphenylcyclopentadiene, tetraphenylcyclopentadiene derivatives, tetraphenylcyclobutadiene, tetraphenylcyclobutadiene derivatives, and low molecular weight fluorescent materials such as stilbene, silicon-containing aromatic, oxazole, furoxane, thiazole, tetraarylmethane, thiadiazole, pyrazole, metacyclophane, acetylene and the like. As the low molecular weight fluorescent material, for example, those described in JP-A No. 57-51781, JP-A NO. 59-194393 and the like, and known materials are mentioned.

The hole transporting material which may be contained in the liquid composition includes polyvinylcarbazole and derivatives thereof, polysilane and derivatives thereof, polysiloxane derivatives having an aromatic amine in the side chain or the main chain, pyrazoline derivatives, arylamine derivatives, stilbene derivatives, triphenyldiamine derivatives, polyaniline and derivatives thereof, polythiophene and derivatives thereof, polypyrrole and derivatives thereof, poly(p-phenylenevinylene) and derivatives thereof, poly(2,5-thienylenevinylene) and derivatives thereof, and the like.

The electron transporting material which may be contained in the liquid composition includes oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives; metal complexes of 8-hydroxyquinoline and derivatives thereof; polyquinoline and derivatives thereof, polyquinoxaline and derivatives thereof, polyfluorene and derivatives thereof, and the like.

The stabilizer which may be contained in the liquid composition includes phenol antioxidants, phosphorus antioxidants and the like.

As the additive for adjusting viscosity and/or surface tension which may be contained in the liquid composition, a high molecular weight compound for increasing viscosity (thickening agent), a poor solvent, a low molecular weight compound for lowering viscosity, a surfactant for lowering surface tension, and the like are listed. The poor solvent means a solvent with which the weight of the polymer compound of the present invention dissolved in 1 g of the solvent is 0.1 mg or less.

As the above-described high molecular weight compound, those not disturbing light emission and charge transportation may be permissible, and usually, those which are soluble in the solvent of the liquid composition are mentioned. As the high molecular weight compound, polystyrene of high molecular weight, polymethyl methacrylate of high molecular weight, and the like can be used. The above-described high molecular weight compound has a polystyrene-equivalent weight average molecular weight of preferably 500000 or more, more preferably 1000000 or more. Also a poor solvent can be used as the thickening agent.

As the antioxidant which may be contained in the liquid composition, those not disturbing light emission and charge transportation may be permissible, and usually, compounds which are soluble in the solvent contained in the liquid composition are mentioned. As the antioxidant, phenol antioxidants, phosphorus antioxidants and the like are exemplified. By use of the antioxidant, the preservation stability of the above-described polymer compound and solvent can be improved.

When the liquid composition contains a hole transporting material, the amount of the hole transporting material in the liquid composition is usually 1 to 80 parts by weight, preferably 5 to 60 parts by weight with respect to 100 parts by weight of the liquid composition excluding the solvent. When the liquid composition of the present invention contains an electron transporting material, the amount of the electron transporting material in the liquid composition is usually 1 to 80 parts by weight, preferably 5 to 60 parts by weight with respect to 100 parts by weight of the liquid composition excluding the solvent.

In the case of film formation using this liquid composition in fabricating a polymer light emitting device, it may be advantageous to only remove a solvent by drying after application of the liquid composition, and also in the case of mixing of a charge transporting material and a light emitting material, the same means can be applied, that is, this method is extremely advantageous for production. In drying, drying may be effected under heating at about 50 to 150° C., alternatively, drying may be carried out under a reduced pressure of about $10^{-3}$ Pa.

As the film formation method using the liquid composition, application methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method and the like can be used.

The proportion of a solvent in the liquid composition is usually 1 wt % to 99.9 wt %, preferably 60 wt % to 99.9 wt %, further preferably 90 wt % to 99.8 wt % with respect to the total weight of the liquid composition. Though the viscosity of the liquid composition varies depending on a printing method, the viscosity at 25° C. is preferably in the range of 0.5 to 500 mPa·s, and when a liquid composition passes through a discharge apparatus such as in an inkjet print method and the like, the viscosity at 25° C. is preferably in the range of 0.5 to 20 mPa·s, for preventing clogging and flying curving in discharging.

As the solvent contained in the liquid composition, those capable of dissolving or dispersing components other than the solvent in the composition are preferable. Exemplified as the solvent are chlorine-based solvents such as chloroform, methylene chloride, 1,2-dichloroethane, 1,1,2-trichloroethane, chlorobenzene, o-dichlorobenzene and the like, ether solvents such as tetrahydrofuran, dioxane and the like, aromatic hydrocarbon solvents such as toluene, xylene, trimethylbenzene, mesitylene and the like, aliphatic hydrocarbon solvents such as cyclohexane, methylcyclohexane, n-pentane, n-hexane, n-heptane, n-octane, n-nonane, n-decane and the like, ketone solvents such as acetone, methyl ethyl ketone, cyclohexanone and the like, ester solvents such as ethyl acetate, butyl acetate, methyl benzoate, ethylcellosolve acetate and the like, polyhydric alcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin, 1,2-hexane diol and the like and derivatives thereof, alcohol solvents such as methanol, ethanol, propanol, isopropanol, cyclohexanol and the like, sulfoxide solvents such as dimethyl sulfoxide and the like, amide solvents such as N-methyl-2-pyrrolidone, N,N-dimethylformamide, and the like. These solvents may be used singly or in combination of two or more. Among the above-described solvents, one or more organic solvents having a structure containing at least one benzene ring and having a melting point of 0° C. or lower and a boiling point of 100° C. or higher are preferably contained from the standpoint of viscosity, film formability and the like.

Regarding the kind of the solvent, aromatic hydrocarbon solvents, aliphatic hydrocarbon solvents, ester solvents and ketone solvents are preferable from the standpoint of solubility of components other than the solvent in the liquid composition into the solvent, uniformity in film formation, viscosity property and the like, and preferable are toluene, xylene, ethylbenzene, diethylbenzene, trimethylbenzene, mesitylene, n-propylbenzene, i-propylbenzene, n-butylbenzene, isobutylbenzene, s-butylbenzene, anisole, ethoxybenzene, 1-methylnaphthalene, cyclohexane, cyclohexanone, cyclohexylbenzene, bicyclohexyl, cyclohexenylcyclohexanone, n-heptylcyclohexane, n-hexylcyclohexane, methyl benzoate, 2-propylcyclohexanone, 2-heptanone, 3-heptanone, 4-heptanone, 2-octanone, 2-nonanone, 2-decanone, dicyclohexyl ketone and bicyclohexyl methyl benzoate, and it is more preferable to contain at least one of xylene, anisole, mesitylene, cyclohexylbenzene and bicyclohexyl methyl benzoate.

The number of the solvent to be contained in the liquid composition is preferably 2 or more, more preferably 2 to 3, and further preferably 2 from the standpoint of film formability and from the standpoint of device properties and the like.

When two solvents are contained in the liquid composition, one of them may be solid at 25° C. From the standpoint of film formability, it is preferable that one solvent has a boiling point of 180° C. or higher and another solvent has a boiling point of lower than 180° C., and it is more preferable that one solvent has a boiling point of 200° C. or higher and another solvent has a boiling point of lower than 180° C. From the standpoint of viscosity, it is preferable that 0.2 wt % or more of components excepting solvents from the liquid composition are dissolved at 60° C. in solvents, and it is preferable that 0.2 wt % or more of components excepting solvents from the liquid composition are dissolved at 25° C. in one of two solvents.

When three solvents are contained in the liquid composition, one or two of them may be solid at 25° C. From the standpoint of film formability, it is preferable that at least one of three solvents has a boiling point of 180° C. or higher and at least one solvent has a boiling point of 180° C. or lower, and it is more preferable that at least one of three solvents has a boiling point of 200° C. or higher and 300° C. or lower and at least one solvent has a boiling point of 180° C. or lower. From the standpoint of viscosity, it is preferable that 0.2 wt % or more of components excepting solvents from the liquid composition are dissolved at 60° C. in two of three solvents, and it is preferable that 0.2 wt % or more of components excepting solvents from the liquid composition are dissolved at 25° C. in one of three solvents.

When two or more solvents are contained in the liquid composition, the content of a solvent having the highest boiling point is preferably 40 to 90 wt %, more preferably 50 to 90 wt %, and further preferably 65 to 85 wt % with respect to the weight of all solvents contained in the liquid composition, from the standpoint of viscosity and film formability.

<Application>

The polymer compound of the present invention can be used not only as an organic transistor material, but also as a film material, an organic semiconductor material, a light emitting material, an optical material or a solar battery material, and as a conductive material by doping.

The film of the present invention will be illustrated. This film is obtained by using the above-described polymer compound. As the kind of the film, a luminous film, a conductive film and an organic semiconductor film are exemplified.

The luminous film has a light emission quantum yield of preferably 50% or more, more preferably 60% or more and further preferably 70% or more from the standpoint of the luminance and light emission voltage of a device and the like.

The conductive film preferably has a surface resistance of 1 KΩ/□ or less. By doping the film with a Lewis acid, ionic compound or the like, electric conductivity can be enhanced. The surface resistance is more preferably 100 KΩ/□ or less, further preferably 10 KΩ/□ or less.

In the organic semiconductor film, one larger parameter of electron mobility or hole mobility is preferably $10^{-5}$ cm$^2$/V/s or more, more preferably $10^{-3}$ cm$^2$/V/s or more, and further preferably $10^{-1}$ cm$^2$/V/s or more. Using the organic semiconductor film, an organic transistor can be fabricated. For example, by forming the organic semiconductor film on a Si substrate carrying a gate electrode and an insulation membrane made of SiO$_2$ and the like formed thereon, and forming a source electrode and a drain electrode with Au and the like, an organic transistor can be obtained.

Next, a polymer electric field effect type transistor as one embodiment of organic transistors will be described.

The polymer compound of the present invention can be suitably used as a material of a polymer electric field effect type transistor, particularly, as a material of an active layer (organic layer). Regarding the structure of a polymer electric field effect type transistor, it may be usually advantageous that a source electrode and a drain electrode are placed in contact with an active layer obtained by using the polymer compound of the present invention, further, a gate electrode is placed sandwiching an insulation layer in contact with the active layer.

The polymer electric field effect type transistor is usually formed on a supporting substrate. The material of the supporting substrate is not particularly restricted providing that it does not disturb a property as an electric field effect type transistor, and glass substrates and flexible film substrates and plastic substrates can be used.

The polymer electric field effect type transistor can be produced by known methods, for example, a method described in JP-A No. 5-110069.

It is very advantageous and preferable for production to use a polymer compound soluble in an organic solvent, in forming an active layer. As the method of film formation from a solution prepared by dissolving an organic solvent-soluble polymer compound in a solvent, application methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet printing method and the like can be used.

Preferable is an encapsulated polymer electric field effect type transistor obtained by fabricating a polymer electric field effect type transistor, then, encapsulating this. By this, the polymer electric field effect type transistor is blocked from atmospheric air, thereby, lowering of properties of the polymer electric field effect type transistor can be suppressed.

As the encapsulation method, a method of covering with an ultraviolet (UV) hardening resin, a thermosetting resin, an inorganic SiONx membrane and the like, a method of pasting a glass plate or a film with an UV hardening resin, a thermosetting resin or the like, and other methods are mentioned. For effectively performing blocking from atmospheric air, it is preferable that processes after fabrication of a polymer electric field effect type transistor until encapsulation are carried out without exposing to atmospheric air (for example, in dried nitrogen atmosphere, vacuum and the like).

Next, the photoelectric conversion device will be described. The photoelectric conversion device can be used in applications such as a solar battery, an optical sensor and the like. Here, a solar battery which is one embodiment of photoelectric conversion devices will be described.

The polymer compound of the present invention can be suitably used as a material of a solar battery, particularly, as an organic semiconductor layer of a schottky barrier type device utilizing an interface between an organic semiconductor and a metal, or as an organic semiconductor layer of a pn hetero junction type device utilizing an interface between an organic semiconductor and an inorganic semiconductor or between organic semiconductors.

Further, the polymer compound of the present invention can be suitably used as an electron donating polymer or an electron accepting polymer in a bulk hetero junction type device in which the donor-acceptor contact area is increased, or an electron donating conjugated polymer (dispersion supporting body) of an organic photoelectric conversion device using a high molecular weight-low molecular weight complex system, for example, a bulk hetero junction type organic photoelectric conversion device containing a dispersed fullerene derivative as an electron acceptor.

With respect to the structure of the photoelectric conversion device, in the case of a pn hetero junction type device, it is advantageous that a p type semiconductor layer is formed on an ohmic electrode, for example, on ITO, further, an n type semiconductor layer is laminated, and an ohmic electrode is provided thereon.

The photoelectric conversion device is usually formed on a supporting substrate. The material of the supporting substrate is not particularly restricted providing that it does not disturb a property as a photoelectric conversion device, and glass substrates and flexible film substrates and plastic substrates can be used.

The photoelectric conversion device can be produced by known methods, for example, a method described in Synth. Met., 102, 982 (1999), and a method described in Science, 270, 1789 (1995).

Next, the polymer light emitting device of the present invention will be described.

The polymer light emitting device of the present invention has an anode, a cathode, and an organic layer containing the above-described polymer compound and disposed between the anode and the cathode. The above-described organic layer functions as a light emitting layer, a hole transporting layer, a hole injection layer, an electron transporting layer, an electron injection layer or the like. In the polymer light emitting device of the present invention, it is preferable that the above-described organic layer is a light emitting layer.

The polymer light emitting device of the present invention includes (1) a polymer light emitting device having an electron transporting layer disposed between a cathode and a light emitting layer, (2) a polymer light emitting device having a hole transporting layer disposed between an anode and a light emitting layer, (3) a polymer light emitting device having an electron transporting layer disposed between a cathode and a light emitting layer and having a hole transporting layer arranged between an anode and a light emitting layer; and the like.

The following structures a) to d) are exemplified as the structure of the polymer light emitting device of the present invention.
a) anode/light emitting layer/cathode
b) anode/hole transporting layer/light emitting layer/cathode
c) anode/light emitting layer/electron transporting layer/cathode
d) anode/hole transporting layer/light emitting layer/electron transporting layer/cathode
(wherein "/" means adjacent lamination of layers; the same shall apply hereinafter.)

The light emitting layer is a layer having a function of emitting light, the hole transporting layer is a layer having a function of transporting holes, and the electron transporting layer is a layer having a function of transporting electrons. The electron transporting layer and hole transporting layer are collectively called a charge transporting layer. Two or more layers of these light emitting layers, hole transporting layers and electron transporting layers may be independently used.

A hole transporting layer adjacent to a light emitting layer is called an interlayer layer in some cases.

As the method of film formation of a light emitting layer, methods of film formation from a solution are exemplified.

For film formation from a solution, application methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method and the like can be used.

In the case of film formation from a solution using the polymer compound of the present invention in fabricating a polymer light emitting device, it may be advantageous to only remove a solvent by drying after application of this solution, and also in the case of mixing of a charge transporting material and a light emitting material, the same means can be applied, that is, this method is extremely advantageous for production.

The thickness of a light emitting layer shows an optimum value varying depending on a material to be used, and may be advantageously selected so as to give appropriate values of driving voltage and light emission efficiency, and is, usually, 1 nm to 1 µm, preferably 2 nm to 500 nm, and further preferably 5 nm to 200 nm.

In the polymer light emitting device of the present invention, a light emitting material other than the above-described polymer compound may be mixed and used in a light emitting layer. In the polymer light emitting device of the present invention, a light emitting layer containing a light emitting material other than the above-described polymer compound may be laminated with a light emitting layer containing the above-described polymer compound.

As the light emitting material other than the above-described polymer compound, known materials can be used. As the compounds of low molecular weight, naphthalene derivatives, anthracene and derivatives thereof, perylene and derivatives thereof, dyes such as polymethines, xanthenes, coumarins and cyanines, metal complexes of 8-hydroxyquinoline and derivatives thereof, aromatic amines, tetraphenylcyclopentadiene and derivatives thereof, tetraphenylbutadiene and derivatives thereof, and the like can be used. As the above-described light emitting material, those described in JP-A Nos. 57-51781 and 59-194393 are also exemplified.

When the polymer light emitting device of the present invention contains a hole transporting layer, exemplified as the hole transporting material to be used are the above-described polymer compounds, polyvinylcarbazole and its derivatives, polysilane and its derivatives, polysiloxane derivatives having an aromatic amine on the side chain or main chain, pyrazoline derivatives, arylamine derivatives, stilbene derivatives, triphenyldiamine derivatives, polyaniline and its derivatives, polythiophene and its derivatives, polypyrrole and its derivatives, poly(p-phenylenevinylene) and its derivatives, poly(2,5-thienylenevinylene) and its derivatives, and the like. As the hole transporting material other than the above-described polymer compound, those described in JP-A Nos. 63-70257, 63-175860, 2-135359, 2-135361, 2-209988, 3-37992 and 3-152184 are also exemplified.

Among them, preferable as the hole transporting material used in a hole transporting layer are high molecular weight hole transporting materials such as polyvinylcarbazole and its derivatives, polysilane and its derivatives, polysiloxane derivatives having an aromatic amine compound group on the side chain or main chain, polyaniline and its derivatives, polythiophene and its derivatives, poly(p-phenylenevinylene) and its derivatives, poly(2,5-thienylenevinylene) and its derivatives, and the like, and further preferable are polyvinylcarbazole and its derivatives, polsilane and its derivatives, and polysiloxane derivatives having an aromatic amine on the side chain or main chain. In the case of a low molecular weight hole transporting material, it is preferable that the hole transporting material is dispersed in a polymer binder in use.

Polyvinylcarbazole and its derivative are obtained, for example, from a vinyl monomer by cation polymerization or radical polymerization.

As the polysilane and its derivative, compounds described in Chemical Review (Chem. Rev.), vol. 89, p. 1359 (1989) and GB Patent No. 2300196 publication are exemplified. Also as the synthesis method, methods described in them can be used, and particularly, the Kipping method is suitably used.

In the polysiloxane derivative, the siloxane skeleton structure shows little hole transportability, thus, those having a structure of the above-mentioned low molecular weight hole transporting material on the side chain or main chain are suitably used. Particularly, those having an aromatic amine showing hole transportability on the side chain or main chain are exemplified.

Regarding the film formation method of a hole transporting layer, in the case of a low molecular weight hole transporting material, a method of film formation from a mixed solution with a polymer binder is exemplified, and in the case of a high molecular weight hole transporting material, a method of film formation from a solution is exemplified.

The solvent to be used for film formation from a solution may be advantageously one which dissolves a hole transporting material. Exemplified as the solvent are chlorine-based solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, ester solvents such as ethyl acetate, butyl acetate, ethylcellosolve acetate and the like.

As the film formation method from a solution, there can be used application methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet print method and the like from a solution.

As the polymer binder to be mixed, those not extremely disturbing charge transportation are preferable, and those showing no strong absorption against visible light are suitably used. Exemplified as the polymer binder are polycarbonate, polyacrylate, polymethyl acrylate, polymethyl methacrylate, polystyrene, polyvinyl chloride and polysiloxane.

Regarding the thickness of a hole transporting layer, the optimum value varies depending on a material to be used, and it may be advantageously selected so that the driving voltage and light emission efficiency become optimum, and a thickness causing no formation of pin holes is necessary, and when the thickness is too large, the driving voltage of a device increases undesirably. Therefore, the thickness of the hole transporting layer is usually 1 nm to 1 µm, preferably 2 nm to 500 nm, and further preferably 5 nm to 200 nm.

When the polymer light emitting device of the present invention has an electron transporting layer, exemplified as the electron transporting material to be used are the above-described polymer compounds, oxadiazole derivatives, anthraquinodimethane and its derivatives, benzoquinone and its derivatives, naphthoquinone and its derivatives, anthraquinone and its derivatives, tetracyanoanthraquinodimethane and its derivatives, fluorenone derivatives, diphenyldicyanoethylene and its derivatives, diphenoquinone derivatives, metal complexes of 8-hydroxyquinoline and its derivatives, polyquinoline and its derivatives, polyquinoxaline and its derivatives, polyfluorene and its derivatives, and the like. As the electron transporting material other than the above-described polymer compound, those described in JP-A Nos. 63-70257, 63-175860, 2-135359, 2-135361, 2-209988, 3-37992 and 3-152184, and the like are also exemplified.

Of them, oxadiazole derivatives, benzoquinone and its derivatives, anthraquinone and its derivatives, metal complexes of 8-hydroxyquinoline and its derivatives, polyquinoline and its derivatives, polyquinoxaline and its derivatives, polyfluorene and its derivatives are preferable, and 2-(4-biphenylyl)-5-(4-t-butylphenyl)-1,3,4-oxadiazole, benzoqinone, anthraquinone, tris(8-quinolinol)aluminum and polyquinoline are further preferable.

A the film formation method of an electron transporting layer, a vacuum vapor-deposition method from a powder and a method of film formation from a solution or melted state are exemplified in the case of an electron transporting material of low molecular weight, and a method of film formation from a solution or melted state is exemplified in the case of an electron transporting material of high molecular weight, respectively. In film formation from a solution or melted state, a polymer binder may also be used together.

The solvent to be used for film formation from a solution may be advantageously one which dissolves an electron transporting material and/or a polymer binder. Exemplified as the solvent are chlorine-based solvents such as chloroform, methylene chloride, dichloroethane and the like, ether solvents such as tetrahydrofuran and the like, aromatic hydrocarbon solvents such as toluene, xylene and the like, ketone solvents such as acetone, methyl ethyl ketone and the like, ester solvents such as ethyl acetate, butyl acetate, ethylcellosolve acetate and the like.

As the film formation method from a solution or melted state, application methods such as a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet printing method and the like can be used.

As the polymer binder to be mixed, those not extremely disturbing charge transportation are preferable, and those showing no strong absorption against visible light are suitably used. Exemplified as the polymer binder are poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride and polysiloxane.

Regarding the thickness of an electron transporting layer, the optimum value varies depending on a material to be used, and it may be advantageously selected so that the driving voltage and light emission efficiency become optimum, and a thickness causing no formation of pin holes is necessary, and when the thickness is too large, the driving voltage of a device increases undesirably. Therefore, the thickness of the electron transporting layer is usually 1 nm to 1 µm, preferably 2 nm to 500 nm, and further preferably 5 nm to 200 nm.

Among charge transporting layers disposed adjacent to an electrode, those having a function of improving charge injection efficiency from an electrode and having an effect of lowering the driving voltage of a device are, in particular, called a charge injection layer (hole injection layer, electron injection layer) in some cases.

Further, for improving close adherence with an electrode or improving charge injection from an electron, the above-mentioned charge injection layer or insulation layer may be arranged adjacent to the electrode, alternatively, for improving close adherence of an interface or preventing mixing, a thin buffer layer may be inserted into an interface of a charge transporting layer and a light emitting layer.

The order and number of layers to be laminated, and the thickness of each layer may be appropriately determined in view of light emission efficiency and device life.

In the present invention, as the polymer light emitting device carrying a disposed charge injection layer (electron injection layer, hole injection layer), mentioned are polymer light emitting devices having a charge injection layer disposed adjacent to a cathode and polymer light emitting devices having a charge injection layer disposed adjacent to an anode.

The following structures e) to p) are mentioned as the structure of the polymer light emitting device of the present invention.

e) anode/charge injection layer/light emitting layer/cathode f) anode/light emitting layer/charge injection layer/cathode g) anode/charge injection layer/light emitting layer/charge injection layer/cathode h) anode/charge injection layer/hole transporting layer/light emitting layer/cathode i) anode/hole transporting layer/light emitting layer/charge injection layer/cathode j) anode/charge injection layer/hole transporting layer/light emitting layer/charge injection layer/cathode k) anode/charge injection layer/light emitting layer/charge transporting layer/cathode l) anode/light emitting layer/electron transporting layer/charge injection layer/cathode m) anode/charge injection layer/light emitting layer/electron transporting layer/charge injection layer/cathode n) anode/charge injection layer/hole transporting layer/light emitting layer/charge transporting layer/cathode o) anode/hole transporting layer/light emitting layer/electron transporting layer/charge injection layer/cathode p) anode/charge injection layer/hole transporting layer/light emitting layer/electron transporting layer/charge injection layer/cathode As the charge injection layer, exemplified are a layer containing an electric conductive polymer, a layer disposed between an anode and a hole transporting layer and containing a material having ionization potential of a value between an anode material and a hole transporting material contained in a hole transporting layer, and a layer disposed between a cathode and an electron transporting layer and containing a material having electron affinity of a value between a cathode material and an electron transporting material contained in an electron transporting layer.

When the above-mentioned charge injection layer contains an electric conductive polymer, the electric conductivity of the electric conductive polymer is preferably $10^{-5}$ S/cm or more and $10^3$ S/cm or less, and for decreasing leak current between light emission picture elements, more preferably $10^{-5}$ S/cm or more and $10^2$ S/cm or less, and further preferably $10^{-5}$ S/cm or more and $10^2$ S/cm or less. Usually, for controlling the electric conductivity of the electric conductive polymer to $10^{-5}$ S/cm or more and $10^3$ S/cm or less, the electric conductive polymer is doped with a suitable amount of ions.

As the kind of ions to be doped, an anion is used in the case of a hole injection layer and a cation is used in the case of an electron injection layer. The anion includes a polystyrenesulfonic ion, an alkylbenzenesulfonic ion, a camphorsulfonic ion and the like, and the cation includes a lithium ion, a sodium ion, a potassium ion, a tetrabutylammonium ion and the like.

The thickness of the charge injection layer is usually 1 nm to 100 nm, preferably 2 nm to 50 nm.

The material to be used in the charge injection layer may be appropriately selected depending on a relation with materials of an electrode and an adjacent layer, and exemplified are the above-described polymer compound, electric conductive polymers such as polyaniline and its derivatives, polythiophene and its derivatives, polypyrrole and its derivatives, polyphenylenevinylene and its derivatives, polythienylenevinylene and its derivatives, polyquinoline and its derivatives, polyquinoxaline and its derivatives, polymers containing an aromatic amine structure on the main chain or side chain, and the like, and metal phthalocyanines (copper phthalocyanine and the like), carbon and the like.

The insulation layer has a function of making charge injection easy. The average thickness of this insulation layer is usually 0.1 to 20 nm, preferably 0.5 to 10 nm, more preferably 1 to 5 nm. As the material of the insulation layer, metal fluorides, metal oxides, organic insulating materials and the like are mentioned. As the polymer light emitting device carrying an insulation layer provided thereon, there are mentioned polymer light emitting devices in which an insulation layer is disposed adjacent to a cathode, and polymer light emitting devices in which an insulation layer is disposed adjacent to an anode.

The following structures q) to ab) are mentioned as the structure of the polymer light emitting device of the present invention.

q) anode/insulation layer/light emitting layer/cathode r) anode/light emitting layer/insulation layer/cathode s) anode/insulation layer/light emitting layer/insulation layer/cathode t) anode/insulation layer/hole transporting layer/light emitting layer/cathode u) anode/hole transporting layer/light emitting layer/insulation layer/cathode v) anode/insulation layer/hole transporting layer/light emitting layer/insulation layer/cathode w) anode/insulation layer/light emitting layer/electron transporting layer/cathode x) anode/light emitting layer/electron transporting layer/insulation layer/cathode y) anode/insulation layer/light emitting layer/electron transporting layer/insulation layer/cathode z) anode/insulation layer/hole transporting layer/light emitting layer/electron transporting layer/cathode aa) anode/hole transporting layer/light emitting layer/electron transporting layer/insulation layer/cathode ab) anode/insulation layer/hole transporting layer/light emitting layer/electron transporting layer/insulation layer/cathode The substrate which forms a polymer light emitting device of the present invention may advantageously be one which does not change in forming an electrode and in forming a layer of an organic substance, and substrates of glass, plastic, polymer film, silicon and the like are exemplified. In the case of an opaque substrate, it is preferable that the opposite electrode is transparent or semi-transparent.

In the present invention, it is usually preferable that at least one of electrodes consisting of an anode and cathode is transparent or semi-transparent, and the anode side is transparent or semi-transparent.

As the material of the anode, an electric conductive metal oxide membrane, a semi-transparent metal film and the like are used. Specifically, membranes (NESA and the like) formed by using electric conductive inorganic compounds composed of indium oxide, zinc oxide, tin oxide, and composite thereof: indium•tin•oxide (ITO), indium•zinc•oxide and the like, and gold, platinum, silver, copper and the like are used, and ITO, indium.zinc.oxide and tin oxide are preferable. As the fabrication method, a vacuum vapor-deposition method, a sputtering method, an ion plating method, a plating method and the like are mentioned. As the anode, organic transparent electric conductive membranes made of polyaniline and its derivatives, polythiophene and its derivatives, and the like may be used.

The thickness of an anode can be selected in view of light transmission and electric conductivity, and it is usually 10 nm to 10 μm, preferably 20 nm to 1 μm, and further preferably 50 nm to 500 nm.

For making electric charge injection easy, a layer made of a phthalocyanine derivative, an electric conductive polymer, carbon and the like, or a layer made of a metal oxide, a metal fluoride, an organic insulation material and the like, may be provided on an anode.

As the material of a cathode, materials of small work function are preferable. Metals such as lithium, sodium, potassium, rubidium, cesium, beryllium, magnesium, calcium, strontium, barium, aluminum, scandium, vanadium, zinc, yttrium, indium, cerium, samarium, europium, terbium, ytterbium and the like, alloys composed of two or more of them, or alloys composed of at least one of them and at least one of gold, silver, platinum, copper, manganese, titanium, cobalt, nickel, tungsten and tin, graphite or graphite intercalation compounds and the like are used, as the cathode material. Examples of the alloy include a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy. The cathode may take a laminated structure consisting of two or more layers.

The thickness of a cathode can be selected in view of electric conductivity and durability, and it is usually 10 nm to 10 μm, preferably 20 nm to 1 μm, and further preferably 50 nm to 500 nm.

As the cathode fabrication method, a vacuum vapor-deposition method, a sputtering method, a lamination method of thermally press-binding a metal film, and the like are used. A layer made of an electric conductive polymer, or a layer made of a metal oxide, a metal fluoride, an organic insulation material and the like, may be provided between a cathode and an organic substance layer, and after fabrication of a cathode, a protective layer for protecting the polymer light emitting device may be installed. For use of the polymer light emitting device stably for a long period of time, it is preferable to install a protective layer and/or protective cover, for protecting a device from outside.

As the protective layer, resins, metal oxides, metal fluorides, metal borides and the like can be used. As the protective cover, a glass plate, and a plastic plate having a surface which has been subjected to low water permeation treatment, and the like can be used, and a method in which the cover is pasted to a device substrate with a thermosetting resin or a photo-curing resin to attain sealing is suitably used. When a space is kept using a spacer, blemishing of a device can be prevented easily. If an inert gas such as nitrogen, argon and the like is filled in this space, oxidation of a cathode can be prevented, further, by placing a drying agent such as barium oxide and the like in this space, it becomes easy to suppress moisture adsorbed in a production process from imparting a damage to the device. It is preferable to adopt at least one strategy among these methods.

The polymer light emitting device of the present invention can be used for a planar light source, and displays such as a segment display, a dot matrix display, a liquid crystal display (for example, back light and the like).

For obtaining light emission in the form of plane using the polymer light emitting device of the present invention, it may be advantages to place a planar anode and a planar cathode so as to overlap. For obtaining light emission in the form of pattern, there are a method in which a mask having a window in the form of pattern is placed on the surface of the above-mentioned planar light emitting device, a method in which an organic substance layer in non-light emitting parts is formed with extremely large thickness to give substantially no light emission, a method in which either anode or cathode, or both electrodes are formed in the form pattern. By forming a pattern by any of these methods, and placing several electrodes so that on/off is independently possible, a display of segment type is obtained which can display digits, letters, simple marks and the like. Further, for providing a dot matrix device, it may be permissible that both an anode and a cathode are formed in the form of stripe, and placed so as to cross. By using a method in which several polymer compounds showing different emission colors are painted separately or a method in which a color filter or a fluorescence conversion filter is used, partial color display and multi-color display are made possible. In the case of a dot matrix device, passive driving is possible, and active driving may be carried out in combination with TFT and the like. These display devices can be used as a display of a computer, a television, a portable terminal, a cellular telephone, a car navigation, a view finder of a video camera, and the like.

Further, the above-mentioned planar light emitting device is of self emitting and thin type, and can be suitably used as a planar light source for back light of a liquid crystal display, or as a planar light source for illumination. If a flexible substrate is used, it can also be used as a curved light source or display.

EXAMPLES

Examples will be shown below for illustrating the present invention further in detail, but the present invention is not limited to them.

For number average molecular weight and weight average molecular weight, the polystyrene-equivalent number average molecular weight and weight average molecular weight were measured by size exclusion chromatography (SEC) (manufactured by Shimadzu Corporation, trade name: LC-10 Avp). A polymer compound to be measured was dissolved in tetrahydrofuran so as to give a concentration of about 0.5 wt %, and 30 μL of the solution was injected into SEC. Tetrahydrofuran was used as the mobile phase of SEC, and allowed to flow at a flow rate of 0.6 mL/min. As the column, two TSKgel Super HM-H (manufactured by Tosoh Corp.) and one TSKgel Super H2000 (manufactured by Tosoh Corp.) were connected serially. A differential refractive index detector (manufactured by Shimadzu Corp., trade name: RID-10A) was used as a detector.

Example 1

Synthesis of Compound M-1

A compound M-1 was synthesized by the following reaction. The process will be illustrated in turn below.

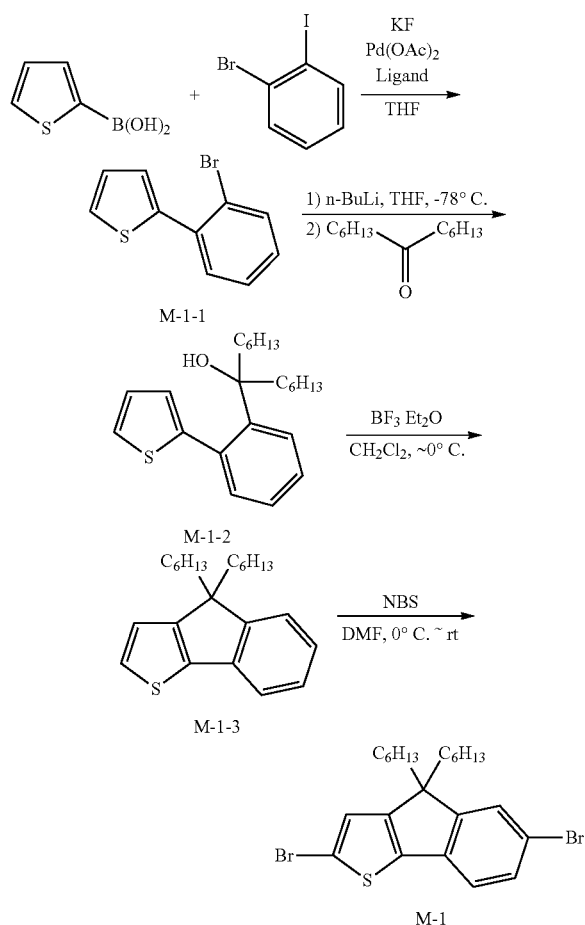

Synthesis of Compound M-1-1

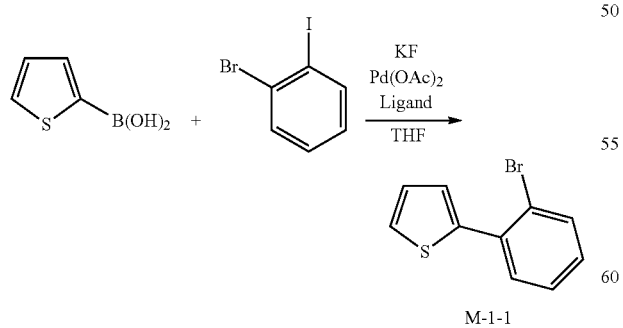

Under an inert atmosphere, into a 1 L four-necked flask was charged 9.20 g (72 mmol) of 2-thiopheneboronic acid, 22.63 g (80 mmol) of 1-bromo-2-iodobenzene, 0.186 g (0.8 mmol) of palladium acetate, 0.479 g (1.6 mmol) of (2-biphenyl)-di-tert-butylphosphine and 14.0 g (240 mmol) of potassium fluoride, and these were dissolved in 300 mL of tetrahydrofuran which had been deaerated for 30 minutes, and the mixture was stirred at room temperature. Three hours after, water (200 mL) was added to stop the reaction, then, the organic layer was extracted with 200 mL of tetrahydrofuran. The resultant organic layer was washed with water and saturated saline, and dried over anhydrous magnesium sulfate. The drying agent was filtrated, then, the solvent was distilled off to obtain a crude product and it was then purified by silica gel column chromatography (eluent: hexane) to obtain 14.37 g (yield: 75%) of a compound M-1-1 as a yellow oil.

Synthesis of Compound M-1-2

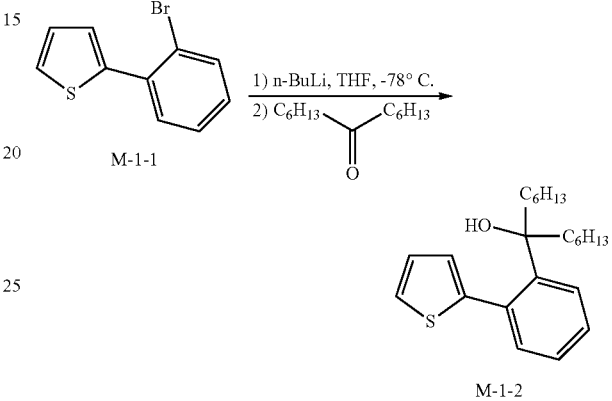

Under an inert atmosphere, into a 100 mL four-necked flask was charged the compound M-1-1 (4.78 g, 0.02 mol) and 40 mL of diethyl ether and the mixture was cooled down to −78° C. A 1.6 M hexane solution of n-butyllithium (15 mL, 0.024 mol) was added and the mixture was stirred for 1.5 hours. Thereafter, 7-tridecanone (4.13 g, 0.021 mol) was added and the mixture was stirred at room temperature for 2 hours. After completion of the reaction, 10 mL of water was added to stop the reaction, and the organic layer was extracted, further, hexane was added to the aqueous layer and extraction thereof was performed to obtain an organic layer which was combined with the above-described organic layer and dried over magnesium sulfate, then, concentrated. The resultant liquid was purified by silica gel column chromatography (hexane solvent), to obtain 4.05 g (yield: 56%) of a compound M-1-2. The above-described operation was repeated several times.

Synthesis of Compound M-1-3

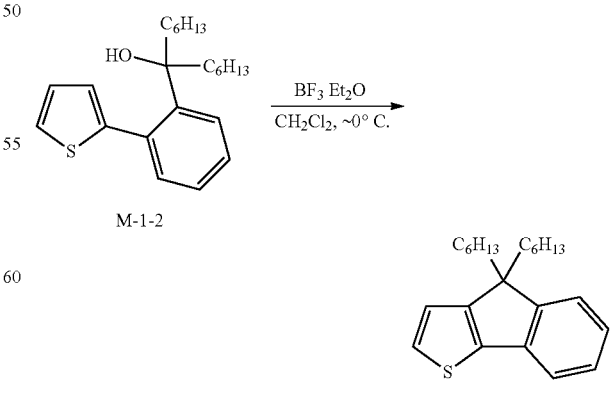

Under an inert atmosphere, into a 500 mL four-necked flask was charged a boron trifluoride-diethyl ether solution (90 mL, 0.6 mol) and the solution was stirred in an ice cool. A dichloromethane solution (800 mL) of the compound M-1-2 (12.9 g, 30 mmol) was dropped from a dropping funnel over a period of 1 hour. After dropping, the ice bath was removed and the mixture was stirred at room temperature for 4 hours. After completion of the reaction, 300 mL of ice water was added to cause separation of an organic layer and an aqueous layer, further, dichloromethane was added to the aqueous layer and extraction thereof was performed to obtain an organic layer which was combined with the above-described organic layer and washed with saturated saline. After drying over magnesium sulfate, filtration was performed and the solvent was distilled off, to obtain 7.03 g (yield: 69%) of a compound M-1-3.

Synthesis of Compound (M-1)

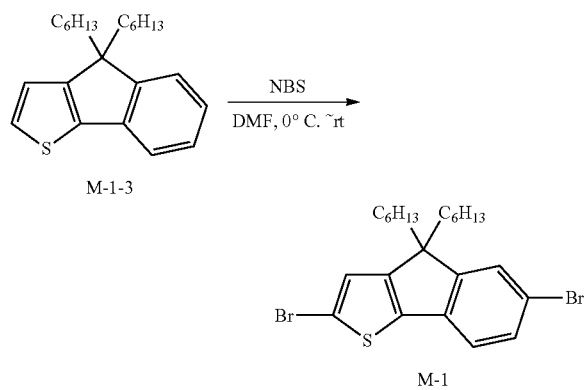

Under an inert atmosphere, into a 100 mL three-necked flask was charged the compound M-1-3 (3.40 g, 10 mmol) and 60 mL of dimethylformamide and the mixture was stirred at 0° C. (in an ice bath). A dimethylformamide solution (80 mL) of N-bromosuccinimide (3.55 g, 20 mmol) was dropped over a period of 30 minutes from a dropping funnel. After completion of dropping, the mixture was stirred at 0° C. for 2 hours, further, heated up to room temperature and stirred for 1 hour. Thereafter, 1.2 g (6.7 mmol) of N-bromosuccinimide was additionally added and the mixture was further stirred for 5 hours, then, 100 mL of a sodium thiosulfate aqueous solution was added. Chloroform was added to cause separation of an organic layer and an aqueous layer, and the organic layer was dried over magnesium sulfate, then, filtration was performed and the solvent was distilled off. The resultant reaction mixture was purified by silica gel column chromatography twice, to obtain 1.42 g (yield: 29%) of a compound M-1.

Example 2

Synthesis of Polymer Compound <P-1>

The compound M-1 (1.02 g) was mixed with 2,7-bis(1,3,2-dioxaborolan-2-yl)-9,9-dioctylfluorene (1.06 g), palladium acetate (1.2 mg), tri(2-methoxyphenyl)phosphine (4.5 mg), trioctylmethyl ammonium chloride (0.28 g, trade name: Aliquat336, manufactured by Aldrich) and toluene (20 mL), and the resultant reaction solution was heated up to 105° C. Next, a 2 M sodium carbonate aqueous solution (5.4 mL) was dropped into the above-described reaction solution, and the mixture was refluxed for 9 hours, then, phenylboronic acid (256 mg) was added, and the mixture was further refluxed for 3 hours. Then, to the above-described reaction solution was added a 1.8 M sodium diethyldithiacarbamate aqueous solution (12 mL), and the mixture was stirred at 80° C. for 2 hours. Thereafter, the reaction solution was cooled down to 25° C., then, washed with water (30 mL) twice, with a 3 wt % acetic acid aqueous solution (30 mL) twice, and with water (30 mL) twice, and purified by passing through an alumina column and a silica gel column, to obtain a toluene solution. The resultant toluene solution was dropped into methanol (300 mL), and the mixture was stirred for 1 hour, then, the resultant solid was filtrated and dried, to obtain a polymer compound <P-1> composed of a repeating unit represented by the following formula:

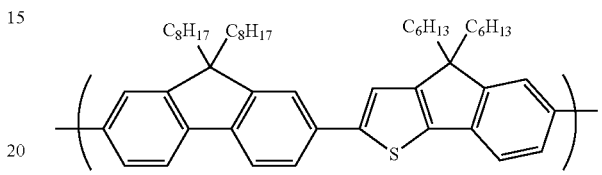

The yielded amount of the resultant polymer compound <P-1> was 1.02 g. The polymer compound <P-1> had a polystyrene-equivalent weight average molecular weight of $5.1 \times 10^4$ and a polystyrene-equivalent number average molecular weight of $2.4 \times 10^4$.

Comparative Example 1

Synthesis of Polymer Compound <P-2>

A polymer compound <P-2> composed of a repeating unit represented by the following formula was polymerized.

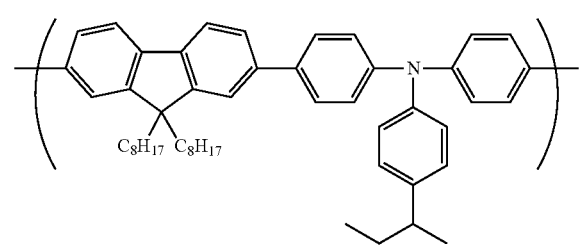

Under an inert atmosphere, 2,7-bis(1,3,2-dioxaborolan-2-yl)-9,9-dioctylfluorene (5.20 g), bis(4-bromophenyl)-(4-secondary-butylphenyl)-amine (4.50 g), palladium acetate (2.2 mg), tri(2-methylphenyl)phosphine (15.1 mg), trioctylmethyl ammonium chloride (0.91 g, trade name: Aliquat336, manufactured by Aldrich) and toluene (70 ml) were mixed and heated up to 105° C. A 2 M sodium carbonate aqueous solution (19 ml) was dropped into this reaction solution, and the mixture was refluxed for 4 hours. After the reaction, phenylboronic acid (121 mg) was added, and the mixture was further refluxed for 3 hours. Then, a sodium diethyldithiacarbamate aqueous solution was added, and the mixture was stirred at 80° C. for 4 hours. After cooling, the mixture was washed with water (60 mL) three times, with a 3 wt % acetic acid aqueous solution (60 mL) three times, and with water (60 mL) three times, and purified by passing through an alumina column and a silica gel column. The resultant toluene solution was dropped into methanol (3 L), and the mixture was stirred for 3 hours, then, the resultant solid was filtrated and dried. The yield of the resultant polymer compound <P-2> was 5.25 g. The polymer compound <P-2> had a polystyrene-equivalent weight average molecular weight of $3.51 \times 10^5$.

Example 3

The surface of an n type silicon substrate doped with antimony at high concentration as a gate electrode was thermally oxidized, thereby forming a 200 nm silicon oxide film (insulation layer). The resultant substrate was ultrasound-washed with acetone for 10 minutes, then, irradiated with ozone UV (ultraviolet intensity: 28 mW/cm$^2$) for 30 minutes. Thereafter, the substrate was immersed for 15 hours in an octane-diluted solution of octadecyltrichlorosilane (ODTS) in a glove box filled with nitrogen, to obtain a silane-treated substrate 1.

Next, the polymer compound <P-1> was dissolved in a solvent chloroform, to obtain a solution having a concentration of 0.5 wt % (organic semiconductor composition), and this was filtrated through a membrane filter having a pore size of 0.2 μm, to prepare a coating solution.

The resultant coating solution was coated on the above-described ODTS layer by a spin coat method to form an active layer having a thickness of about 60 nm, then, a source electrode and a drain electrode having a channel length of 20 μm and a channel width of 2 mm were formed on the active layer by a vacuum vapor deposition method using a metal mask, thereby fabricating an electric field effect-type organic film transistor 1.

The electric field effect-type organic film transistor 1 was subjected to measurement of its transistor property under conditions of a gate voltage Vg changing from 0 to −60 V and an inter-source-drain voltage Vsd changing from 0 to −60 V, and an excellent transistor motion was confirmed. A drain current of 3.9 μA was obtained at Vg=−50 V and Vsd=−50 V, as a transmission property. From this property, the electric field effect mobility was calculated to 6.5×10$^{-3}$ cm$^2$/Vs.

Comparative Example 2

Next, an electric field effect-type organic film transistor 2 was fabricated in the same manner as in Example 3 excepting that the polymer compound <P-2> was used instead of the polymer compound <P-1>, and its transistor property was measured. By this measurement, a drain current of 1.4 μA was obtained at Vg=−50 V and Vsd=−50 V, as a transmission property. From this property, the electric field effect mobility was calculated to 1.5×10$^{-3}$ cm$^2$/Vs.

Industrial Applicability

When the polymer compound of the present invention is used in an electric field effect-type organic transistor, its electric field effect mobility increases, thus, this compound is industrially extremely useful.

The invention claimed is:

1. A polymer compound comprising a repeating unit represented by the formula (I):

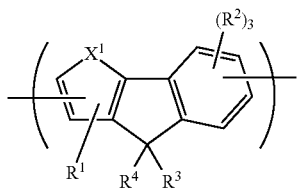

wherein X$^1$ represents an oxygen atom, a sulfur atom or —N(R$^N$)—, R$^1$, R$^2$ and R$^N$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group, R$^3$ and R$^4$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group, and plurality of R$^2$s may be the same or mutually different.

2. The polymer compound according to claim 1, wherein the repeating unit represented by the formula (I) is a repeating unit represented by the formula (II):

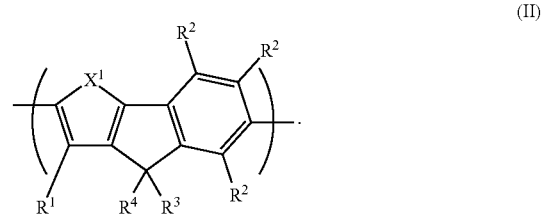

3. The polymer compound according to claim 1, wherein R$^1$ and R$^2$ represent a hydrogen atom.

4. The polymer compound according to claim 1, wherein X$^1$ represents a sulfur atom.

5. The polymer compound according to claim 1, comprising the repeating unit represented by the formula (I) in an amount of 30 to 100 mol %.

6. The polymer compound according to claim 1, further comprising a repeating unit represented by the formula (III):

—(Ar$^1$)—    (III)

wherein Ar$^1$ represents an arylene group, a di-valent heterocyclic group or a di-valent aromatic amine residue.

7. The polymer compound according to claim 6, wherein the arylene group represented by Ar$^1$ is a group represented by the formula (IV):

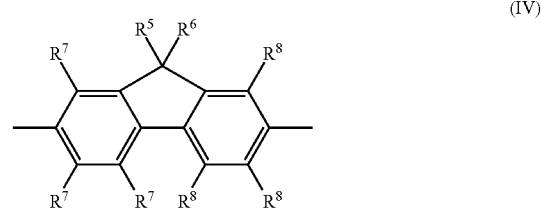

wherein R$^5$ and R$^6$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group, $R^7$ and $R^8$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group, plurality of $R^7$s may be the same or mutually different, and a plurality of $R^8$s may be the same or mutually different.

8. The polymer compound according to claim 1, having a polystyrene-equivalent weight average molecular weight of $1 \times 10^3$ to $1 \times 10^8$.

9. A composition comprising the polymer compound according to claim 1.

10. A film comprising the polymer compound according to claim 1.

11. A polymer light emitting device comprising an anode, a cathode, and an organic layer containing the polymer compound according to claim 1 disposed between the anode and the cathode.

12. The polymer light emitting device according to claim 11, wherein the organic layer is a light emitting layer.

13. An organic transistor comprising a source electrode, a drain electrode, a gate electrode, and an organic layer containing the polymer compound according to claim 1.

14. A photoelectric conversion device comprising an anode, a cathode, and an organic layer containing the polymer compound according to claim 1 disposed between the anode and the cathode.

15. A method of producing a compound represented by the formula (M-1-3a), comprising a first step of reacting a compound represented by the formula (M-1-1a) and a compound represented by the formula (M-1-1b) to produce a compound represented by the formula (M-1-2a), and a second step of subjecting the compound represented by the formula (M-1-2a) to a dehydration reaction to produce a compound represented by the formula (M-1-3a),

(M-1-1a)

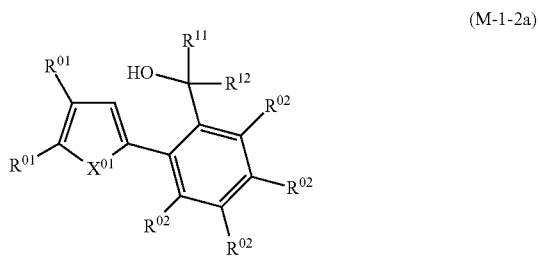

wherein $X^a$ represents a halogen atom, $X^{01}$ represents an oxygen atom, a sulfur atom or —N($R^{NN}$)—, $R^{01}$, $R^{02}$ and $R^{NN}$ represent each independently a hydrogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, a substituted amino group, a silyl group, a substituted silyl group, an imine residue, an acid imide group, a cyano group or a nitro group, and plurality of $R^{01}$s may be the same or mutually different, and a plurality of $R^{02}$s may be the same or mutually different, $$R^{11}—C(=O)—R^{12} \quad (M\text{-}1\text{-}1b)$$

wherein $R^{11}$ and $R^{12}$ represent each independently a hydrogen atom, an alkyl group, an alkenyl group, an alkynyl group, an alkylthio group, an aryl group, an arylthio group, an arylalkyl group, an arylalkylthio group, an arylalkenyl group, an arylalkynyl group, a mono-valent heterocyclic group, a heterocyclic thio group, an amino group, a substituted amino group, a silyl group, a substituted silyl group, an imine residue, an amide group, an acid imide group, a cyano group or a nitro group,

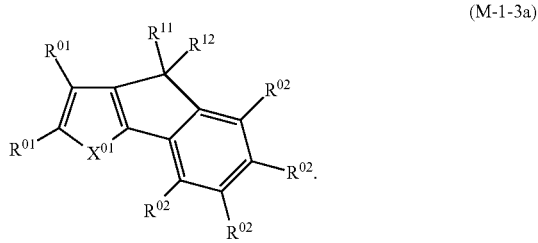

(M-1-2a)

and (M-1-3a)

16. A film comprising the compound represented by the formula (V):

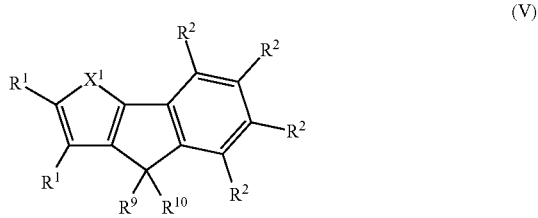

(V)

wherein $X^1$ represents an oxygen atom, a sulfur atom or —N($R^N$)—, $R^1$, $R^2$ and $R^N$ represent each independently a hydrogen atom, a halogen atom, an alkyl group, an alkenyl group, an alkynl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue, an amide group, an acid imide group, a carboxyl group, a substituted carboxyl group, a cyano group or a nitro group, $R^9$ and $R^{10}$ represent each independently a hydrogen atom, a halogen atom, an alkyl group, an alkenyl group, an alkynyl group, an alkoxy group, an alkylthio group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group, plurality of $R^1$s may be the same or mutually different, and a plurality of $R^2$s may be the same or mutually different.

17. A light emitting device comprising an anode, a cathode, and an organic layer containing the compound represented by the formula (V):

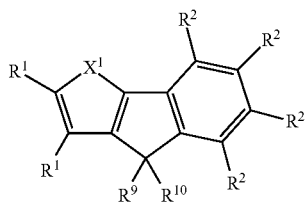

(V)

wherein $X^1$ represents an oxygen atom, a sulfur atom or —N($R^N$)—, $R^1$, $R^2$ and $R^N$ represent each independently a hydrogen atom, a halogen atom, an alkyl group, an alkenyl group, an alkynyl group, an alkoxy group, an alkylthio group, an aryl group, an aryloxy group, an arylthio group, an arylalkyl group, an arylalkoxy group, an arylalkylthio group, an arylalkenyl group, an arylalkynyl group, a mono-valent heterocyclic group, a heterocyclic thio group, an amino group, a substituted amino group, a silyl group, a substituted silyl group, an acyl group, an acyloxy group, an imine residue. an amide group, an acid imide group, a carboxyl group, a substituted carboxyl group, a cyano group or a nitro group, $R^9$ and $R^{10}$ represent each independently a hydrogen atom, a halogen atom, an alkyl group, an alkenyl group, an alkynyl group, an alkoxy group, an alkylthio group, an aryloxy group, an arylthio group, an arylalkyl group, an arylalkoxy group, an arylalkylthio group, an arylalkenyl group, an arylalkynl group, a mono-valent heterocyclic group, a heterocyclic thio group, an amino group, a substituted amino group, a silyl group, a substituted silyl group, an acyl group, an imine residue, an amide group, an acid imide group, a carboxyl group, a substituted carboxyl group, a cyano group or a nitro group, plurality of $R^1$s may be the same or mutually different, and a plurality of $R^2$s may be the same or mutually different, disposed between the anode and the cathode.

* * * * *